US010398631B2

(12) United States Patent
Valverde et al.

(10) Patent No.: US 10,398,631 B2
(45) Date of Patent: Sep. 3, 2019

(54) GEL-TYPE COSMETIC COMPOSITION

(71) Applicant: L'OREAL, Paris (FR)

(72) Inventors: Elodie Valverde, Paris (FR); Véronique Ferrari, Maisons-Alfort (FR); Guillaume Cassin, Villebon sur Yvette (FR); Patrice Styczen, Gif-sur-Yvette (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/770,292

(22) PCT Filed: Feb. 25, 2014

(86) PCT No.: PCT/IB2014/059239
§ 371 (c)(1),
(2) Date: Aug. 25, 2015

(87) PCT Pub. No.: WO2014/128679
PCT Pub. Date: Aug. 28, 2014

(65) Prior Publication Data
US 2016/0008236 A1 Jan. 14, 2016

(30) Foreign Application Priority Data

Feb. 25, 2013 (FR) ...................................... 13 00430

(51) Int. Cl.
A61K 8/26 (2006.01)
A61K 8/04 (2006.01)
A61K 8/25 (2006.01)
A61K 8/34 (2006.01)
A61Q 1/02 (2006.01)
A61K 8/73 (2006.01)
A61Q 19/00 (2006.01)
A61K 8/81 (2006.01)
A61K 8/891 (2006.01)
A61K 8/92 (2006.01)
A45D 40/24 (2006.01)
A61K 8/89 (2006.01)
A61Q 1/06 (2006.01)
A61Q 1/10 (2006.01)
A61Q 1/12 (2006.01)
A61K 8/9706 (2017.01)

(52) U.S. Cl.
CPC .............. A61K 8/042 (2013.01); A45D 40/24 (2013.01); A61K 8/25 (2013.01); A61K 8/26 (2013.01); A61K 8/342 (2013.01); A61K 8/73 (2013.01); A61K 8/732 (2013.01); A61K 8/8111 (2013.01); A61K 8/89 (2013.01); A61K 8/891 (2013.01); A61K 8/92 (2013.01); A61K 8/9706 (2017.08); A61Q 1/02 (2013.01); A61Q 1/06 (2013.01); A61Q 1/10 (2013.01); A61Q 1/12 (2013.01); A61Q 19/00 (2013.01); A61K 2800/43 (2013.01); A61K 2800/591 (2013.01); A61K 2800/87 (2013.01); A61K 2800/882 (2013.01)

(58) Field of Classification Search
None
See application file for complete search history.

(56) References Cited

U.S. PATENT DOCUMENTS

| 5,266,321 | A | 11/1993 | Shukuzaki et al. |
| 5,470,884 | A | 11/1995 | Corless et al. |
| 6,120,780 | A | 9/2000 | Dupuis et al. |
| 6,187,323 | B1 | 2/2001 | Aiache et al. |
| 6,497,861 | B1 | 12/2002 | Wang et al. |
| 6,916,464 | B2 | 7/2005 | Hansenne et al. |
| 7,942,937 | B2 | 5/2011 | Brun |
| 8,216,554 | B2 | 7/2012 | Shah et al. |
| 8,333,956 | B2 | 12/2012 | Brieva et al. |
| 8,449,870 | B2 | 5/2013 | Wang et al. |
| 8,858,967 | B2 | 10/2014 | Astruc et al. |
| 2003/0026772 | A1 | 2/2003 | Jager-Lezer et al. |
| 2003/0223943 | A1 | 12/2003 | Uang et al. |
| 2005/0048016 | A1 | 3/2005 | Lebreton et al. |
| 2005/0163730 | A1 | 7/2005 | Rosevear et al. |
| 2005/0196364 | A1 | 9/2005 | Josso |
| 2007/0231354 | A1 | 10/2007 | Sogabe et al. |
| 2008/0064761 | A1 | 3/2008 | Gondek et al. |
| 2010/0221296 | A1 | 9/2010 | Moneuze et al. |
| 2010/0310481 | A1 | 12/2010 | Chevalier et al. |

(Continued)

FOREIGN PATENT DOCUMENTS

EP   0 388 582 A2   9/1990
EP   0 963 751 A2   12/1999

(Continued)

OTHER PUBLICATIONS

"Bentonite Gel ISD V", 2008, 11 pages. (Year: 2008).*
Feb. 23, 2016 Office Action issued in U.S. Appl. No. 14/770,154.
Jul. 15, 2016 Office Action issued in U.S. Appl. No. 14/770,154.
Technical data sheet. Viscosity of Carbpool Polymers in Aqueous Systems. Lubrizol. 2009. 10p.
Aug. 3, 2016 Office Action issued in U.S. Appl. No. 14/770,182.
Almeida, et al., "Moisturizing Effect of Oleogel/Hydrogel Mixtures", Pharmaceutical Development and Technology, vol. 13, Jan. 2, 2008, pp. 487-494, XP009174126.
May 9, 2014 Written Opinion of the International Searching Authority issued in PCT Patent Application No. PCT/IB2014/059238.
May 9, 2014 International Search Report issued in Patent Application No. PCT/IB2014/059238.

(Continued)

Primary Examiner — Brian Gulledge
(74) Attorney, Agent, or Firm — Oliff PLC

(57) ABSTRACT

Cosmetic composition for making up and/or caring for keratin materials, in particular the skin and/or the lips, including: at least one aqueous phase gelled with at least one polymeric gelling agent that is natural or of natural origin; and at least one oily phase gelled with at least one lipophilic gelling agent chosen from particulate gelling agents, organopolysiloxane elastomers, semi-crystalline polymers and dextrin esters, and mixtures thereof; the phases forming therein a macroscopically homogeneous mixture.

13 Claims, No Drawings

(56) References Cited

U.S. PATENT DOCUMENTS

| | | | |
|---|---|---|---|
| 2010/0322983 A1* | 12/2010 | Griffiths-Brophy ... | A61K 8/044 424/401 |
| 2011/0014139 A1 | 1/2011 | Viala et al. | |
| 2011/0158920 A1* | 6/2011 | Morley ................. | A61K 8/042 424/59 |
| 2017/0189278 A1 | 7/2017 | Bchir et al. | |

FOREIGN PATENT DOCUMENTS

| | | |
|---|---|---|
| EP | 1 818 042 A2 | 8/2007 |
| EP | 2 135 525 A2 | 12/2009 |
| EP | 2 492 333 A1 | 8/2012 |
| FR | 2 986 422 A1 | 8/2013 |
| FR | 2 986 424 A1 | 8/2013 |
| FR | 2 992 203 A1 | 12/2013 |
| JP | S60-6607 A | 1/1985 |
| JP | 2005-112834 A | 4/2005 |
| JP | 2005-232107 A | 9/2005 |
| JP | 2005-314391 A | 11/2005 |
| JP | 2007-217411 A | 8/2007 |
| JP | 2007-527452 A | 9/2007 |
| JP | 2007-262032 A | 10/2007 |
| JP | 2009-502852 A | 1/2009 |
| JP | 2010-006708 A | 1/2010 |
| JP | 2010-111674 A | 5/2010 |
| JP | 2011-088850 A | 5/2011 |
| JP | 2011-213652 A | 10/2011 |
| PT | 2004-05758 A | 9/2006 |
| WO | 99/22696 A1 | 5/1999 |
| WO | 99/62497 A1 | 12/1999 |
| WO | 99/65455 A1 | 12/1999 |
| WO | WO 99/62497 * | 12/1999 |
| WO | WO 99/65455 * | 12/1999 |
| WO | 01/89470 A1 | 11/2001 |
| WO | 2008/081175 A2 | 7/2008 |
| WO | 2008/114732 A1 | 9/2008 |
| WO | 2011-143254 A2 | 11/2011 |
| WO | 2013/087927 A1 | 6/2013 |
| WO | 2013/093869 A2 | 6/2013 |
| WO | 2013/107000 A1 | 7/2013 |
| WO | 2014/128678 A1 | 8/2014 |
| WO | 2014/128680 A1 | 8/2014 |

OTHER PUBLICATIONS

U.S. Appl. No. 14/770,154, filed Aug. 25, 2015 in the name of Veronique et al.
U.S. Appl. No. 14/770,182, filed Aug. 25, 2015 in the name of Valverde et al.
Almeida, et al., "Evaluation of the Physical Stability of Two Oleogels", International Journal of Pharmaceutics, vol. 327, No. 1-2, Dec. 11, 2006, pp. 73-77.
May 15, 2014 Written Opinion of the International Searching Authority issued in PCT Patent Application No. PCT/IB2014/059239.
May 15, 2014 International Search Report issued in Patent Application No. PCT/IB2014/059239.
May 27, 2014 Written Opinion of the International Searching Authority issued in PCT Patent Application No. PCT/IB2014/059240.
May 27, 2014 International Search Report issued in Patent Application No. PCT/IB2014/059240.
Seppic, "Sepinov EMT 10," Apr. 2006, pp. 1-19.
Jan. 19, 2017 Office Action issued in U.S. Appl. No. 14/770,182.
Jan. 9, 2018 Office Action issued in Japanese Application No. 2015-558599.
Jan. 19, 2018 Office Action issued in U.S. Appl. No. 15/314,221.
Oct. 20, 2017 Third Party Observation issued in Japanese Patent Application No. 2015-558600.
Dow Corning VM-2270 (Aerogel Fine Particles (2012) accessed at http://www.dowcorning.com/content/publishedlit/27-1235.pdf accessed Jan. 10, 2018 (Year: 2012)).
Jul. 31, 2015 International Search Report issued in International Patent Application No. PCT/IB2015/053953.
Kobayashi. "Oil Up Cosmetic Material Consist Disperse System Silicone Gel Composition Polysiloxane Powder Base Agent". Sep. 14, 1989. XP002735135.
U.S. Appl. No. 15/507,318, filed Feb. 28, 2017 in the name of Roubot et al.
U.S. Appl. No. 15/314,221, filed Nov. 28, 2016 in the name of Bchir et al.
Jan. 13, 2016 International Search Report issued in International Patent Application No. PCT/IB2015/056474.
Jan. 19, 2016 International Search Report issued in International Patent Application No. PCT/IB2015/056471.
Degussa. "Versatile and Effective", Aerosil. Mar. 3, 2003, p. 1-21. XP003026229.
Apr. 7, 2017 Office Action issued in U.S. Appl. No. 14/770,154.
Jan. 13, 2016 Written Opinion issued in International Patent Application No. PCT/IB2015/056474.
Jan. 19, 2016 Written Opinion issued in International Patent Application No. PCT/IB2015/056471.
May 20, 2015 Written Opinion issued in French Patent Application No. 1458034.
Jul. 31, 2015 Written Opinion issued in International Patent Application No. PCT/IB2015/053953.
Jul. 12, 2017 Office Action issued in U.S. Appl. No. 15/314,221.
Jul. 28, 2017 Office Action issued in U.S. Appl. No. 14/770,182.
U.S. Appl. No. 15/507,440, filed Feb. 28, 2017 in the name of Bouarfa et al.
Elizabeth Arden, "Moister Lotion SPF 15," Mintel, pp. 1-3, Record ID: 639186, Jan. 2007.
Marks & Spencer, "Daly Protect Everyday Moisturiser SPF 12," Mintel, pp. 1-3, Record ID: 1448926, Dec. 2010.
Jul. 4, 2017 Third Party Observation issued in European Application No. 14710991.2.
Jul. 13, 2017 Third Party Observation issued in European Application No. 14708695.3.
Scrubs, "Instant Lifting Cream," Mintel, Record ID: 1912786, pp. 1-3, Nov. 2012.
Jul. 2, 2018 Office Action issued in U.S. Appl. No. 15/507,440.
May 23, 2018 Office Action issued in U.S. Appl. No. 15/507,318.
Apr. 5, 2018 Office Action issued in U.S. Appl. No. 15/507,440.
Apr. 19, 2018 Office Action issued in U.S. Appl. No. 14/770,154.
May 4, 2018 Office Action issue in U.S. Appl. No. 14/770,182.
Oct. 4, 2018 Office Action issued in U.S. Appl. No. 15/314,221.
Dec. 10, 2018 Office Action issued in U.S. Appl. No. 14/770,154.
Dec. 20, 2018 Office Action issued in U.S. Appl. No. 15/507,318.
Annamarya Scaccia, "What Are the Benefits of Using Avocado Oil on My Skin?," Health Line News Letter, Downloaded from https://www.healthline.com/health /beauty-skin-care/ avocado-oil-for-skin on Dec. 14, 2018, (Year 2018).
Unknown Author, "Safety Assessment of Alkoxy Polysiloxane as Used in Cosmetics," released Feb. 21, 2014 (only pertinent portion is provided), (Year 2014).
Mar. 21, 2019 Office Action issued in U.S. Appl. No. 15/507,440.
May 2, 2019 Office Action issued in U.S. Appl. No. 15/314,221.
May 3, 2019 Office Action issued in U.S. Appl. No. 15/507,318.

* cited by examiner

GEL-TYPE COSMETIC COMPOSITION

The present invention is directed towards proposing for the field of caring for and making up keratin materials, especially the skin and/or the lips, and in particular the skin, a novel galenical form that is most particularly advantageous with regard to its technical performance and the sensations it affords the user during its application, in particular to the skin.

The term "keratin materials" especially means the skin, the lips and/or the eyelashes, in particular the skin and/or the lips, and preferably the skin.

Conventionally, a cosmetic composition formulator uses emulsified systems combining an aqueous phase for freshness and an oily phase for comfort. The strong point of these systems is also that they allow the combination, within the same composition, of cosmetic ingredients or active agents that have different affinities with respect to these two aqueous and oily phases.

Unfortunately, these emulsified systems do not lend themselves to rapid and easy production of an infinite range of compositions. Thus, for a given emulsified system, it often proves complicated to functionalize the formulation by adding, for example, an antisun product, certain active agents, pigments, polymers, fragrances or fillers, etc. without impairing the stability, the sensory properties and the quality of the film deposited on the keratin materials and especially the skin. The formulation then needs to be readjusted. It is also difficult to reconcile, within the same composition, opposing technical performance qualities, for instance mattness (which may make the skin dry) and moisturizing (which may make the skin shiny).

Furthermore, emulsified systems do not lend themselves to the formulation of all the ingredients or active agents liable to be considered in the field of care and/or makeup, or even to the formulation of high contents of certain cosmetic ingredients or active agents. Non-compliance with these incompatibilities has the consequence of destabilizing the emulsified architecture, which then, inter alia, undergoes demixing.

Finally, these emulsified systems do not lend themselves to rapid and easy production of an infinite range of textures.

Moreover, in the case of making up the complexion, the preferred emulsifying systems are mainly reverse emulsions with regard to the good level of coverage and the homogeneous appearance they afford when compared with direct emulsions. On the other hand, their weak point is a high greasy and tacky sensation, and thus a lack of lightness as regards the textures obtained.

Galenical formulations of gel/gel type partially meet these expectations (Almeida et al., Pharmaceutical Development and Technology, 2008, 13:487, tables 1 and 2, page 488; WO 99/65455; PI 0405758-9; WO 99/62497; JP 2005-112834 and WO 2008/081175). Formulations of this type combine a gelled aqueous phase with a gelled oily phase. In fact, these gel/gel formulations were essentially proposed as an advantageous alternative to emulsified systems on the grounds that they make it possible to dispense with the use of the surfactants required for the stability and texturization of emulsions. Unfortunately, besides this advantage, the gel/gel formulations described hitherto do not essentially reveal any novel or improved technical performance qualities.

It therefore remains difficult for a person skilled in the art to propose homogeneous compositions that are capable of affording an immediate visual result on the skin with a light sensation on application, this expected immediate result preferentially being good coverage of colour imperfections and/or of relief imperfections, without, however, marking them. It is therefore necessary to find novel systems for distributing on the skin components such as water, fatty substances and solid particles.

These novel architectures must be entirely satisfactory to users as regards the sensation afforded, but must also be capable of affording improved cosmetic properties, or must even have an increased number of technical performance qualities such as freshness, lightness, emollience, comfort, coverage of imperfections, colour, unifying aspect, lightening, etc., and, on the other hand, must be free of the known side effects of oily and aqueous phases such as, respectively, a greasy feel, a tacky feel, a feeling of lack of glidance or alternatively a feeling of dragging on application.

The inventors have now found, unexpectedly, that such an objective can be achieved via the choice of a system of specific hydrophilic gelling agent(s)/lipophilic gelling agent(s) for the preparation of a cosmetic composition of the type such as a bi-continuous but on the other hand macroscopically homogeneous system which has a large number of technical performance qualities and which furthermore has optimized effects.

More precisely, the inventors have found that the choice of a system of specific hydrophilic gelling agent(s)/lipophilic gelling agent(s) makes it possible, contrary to all expectation, to combine in a single composition a significant number of technical performance qualities, with the intensity of each performance quality advantageously not being attenuated by the manifestation of other associated performance qualities, or even being, for certain performance qualities, stimulated.

Thus, according to one of its aspects, the present invention relates to a cosmetic composition for making up and/or caring for keratin materials, in particular the skin and/or the lips, comprising:
  at least one aqueous phase gelled with at least one polymeric gelling agent that is natural or of natural origin; and
  at least one oily phase gelled with at least one lipophilic gelling agent chosen from particulate gelling agents, organopolysiloxane elastomers, semi-crystalline polymers and dextrin esters, and mixtures thereof;
the said phases forming therein a macroscopically homogeneous mixture;
on condition that when the lipophilic gelling agent consists of a trimethyl silica or a crosslinked polymer of dimethicone/vinyl dimethicone, then the polymeric gelling agent which is natural or of natural origin does not consist of 3% or more of potato carboxymethyl starch.

According to one embodiment variant, a composition according to the invention consists of an aqueous phase gelled with at least one polymeric gelling agent that is natural or of natural origin, and an oily phase gelled with at least one lipophilic gelling agent chosen from particulate gelling agents, organopolysiloxane elastomers, semi-crystalline polymers and dextrin esters, and mixtures thereof.

According to a preferred variant, a composition according to the invention also contains at least one dyestuff.

This dyestuff may be chosen from pigments, and water-soluble or liposoluble dyestuffs, especially as detailed below.

In particular, the dyestuffs are pigments.

According to an advantageous embodiment variant, the dyestuff is conveyed at least in the gelled oily phase.

As stated above, the inventors have found, contrary to all expectation, that the choice of particular hydrophilic gelling agent(s)/lipophilic gelling agent(s) couples for texturing a composition of gel/gel type makes it possible to significantly improve certain technical performance qualities, and to dispense with certain adverse effects inherent in the gelling agents under consideration, or even to reconcile within this composition properties which it was hitherto difficult to make coexist. Furthermore, as emerges from the examples below, the present invention moreover makes it possible, unexpectedly, to optimize some of the expected technical performance qualities.

The inventors have also found, surprisingly, that the soft-focus performance quality of a composition according to the invention comprising aqueous and oily phases gelled, respectively, with a polymeric or particulate gelling agent with a soft-focus effect proves to be significantly improved. The gain in soft-focus effect proves to be greater than the sum of the respective optical effects of each of the two gelled phases in each of the two compositions. There is manifestly synergism.

Besides the abovementioned unexpected advantages, the gelling system under consideration according to the invention affords a texture that is sufficiently thickened to be compatible with the formulation of a very wide diversity of ingredients or active agents. It combines in a single formulation a large number of functional active agents or ingredients (fillers, pigments, etc.).

The compositions according to the invention also prove to be very stable and not subject to syneresis.

According to another of its aspects, a subject of the invention is also a process for preparing a cosmetic composition for making up and/or caring for keratin materials, according to the invention, in particular the skin and/or the lips, comprising at least one step of mixing:
  at least one aqueous phase gelled with at least one polymeric gelling agent that is natural or of natural origin; and
  at least one oily phase gelled with at least one lipophilic gelling agent chosen from particulate gelling agents, organopolysiloxane elastomers, semi-crystalline polymers and dextrin esters, and mixtures thereof;
under conditions suitable for obtaining a macroscopically homogeneous mixture.

According to one embodiment variant, this process may advantageously comprise a step of mixing at least three or even more gelled phases.

For obvious reasons, the number of gelled aqueous phases and of gelled oily phases to be considered for forming a composition according to the invention may range for each of the two types of phase beyond two. It is especially conditioned by the number of expected technical performance qualities.

For example, this process may use a single gelled aqueous phase and two oily phases gelled with different lipophilic gelling agents.

Conversely, this process may also use a single gelled oily phase and two aqueous phases gelled with different hydrophilic gelling agents.

For example, the phases having the same architecture, namely aqueous or oily, may be precombined to form a premix, and it is this premix which is placed in contact with the phase or even with a premix of several phases having the other architecture.

The corresponding aqueous and oily gels may be prepared separately and then mixed together without heating, without requiring the necessary presence of surfactants in order to achieve the desired architecture. Thus, in addition to the advantages mentioned above, the claimed compositions may be readily prepared at reduced cost.

Advantageously, the mixing of the phases may be performed at room temperature.

However, the process of the invention may comprise, if necessary, a step of heating the mixture.

The process according to the invention thus offers the formulator a simple and rapid means for gaining access to a multitude of cosmetic compositions having common performance qualities but also performance qualities that are specific to each of its compositions.

The present invention also gives the user access to this faculty of mixing at least two phases of the same architecture with at least one phase of different architecture via the provision of a cosmetic kit for making up and/or caring for keratin materials.

Thus, according to another of its aspects, the present invention relates to a cosmetic kit for making up and/or caring for keratin materials, in particular the skin and/or the lips, comprising, in separate containers, at least one aqueous phase gelled with at least one polymeric gelling agent that is natural or of natural origin; and to at least one oily phase gelled with at least one lipophilic gelling agent chosen from particulate gelling agents, organopolysiloxane elastomers, semi-crystalline polymers and dextrin esters, and mixtures thereof; and also to instructions for using the extemporaneous mixtures.

According to yet another of its aspects, the present invention relates to a device for making up and/or caring for keratin materials, in particular the skin and/or the lips, comprising at least:
  two separate containers containing, respectively, at least one aqueous phase gelled with at least one polymeric gelling agent that is natural or of natural origin; and at least one oily phase gelled with at least one lipophilic gelling agent chosen from particulate gelling agents, organopolysiloxane elastomers, semi-crystalline polymers and dextrin esters, and mixtures thereof;
  a distinct chamber for mixing the said containers, comprising an aperture configured to allow the introduction of the said phases to be mixed; and
  a means for distributing a macroscopically homogeneous mixture of the two phases.

According to an advantageous variant, the kits and devices according to the invention contain at least two, or even more, different gelled phases for each of the two types of aqueous and oily architecture.

According to a particular embodiment, the representative gelled phases of the same type of architecture are gelled with a different gelling agent.

Multi-phase formulations of "patchwork" type may thus be developed.

According to another particular embodiment, the representative gelled phases of the same type of architecture are different as regards their optical properties. For example, the kit or device may propose two oily gelled phases textured by the same oily gelling agent, but one containing dyestuffs and the other not. The user thus has the possibility of exploiting or not exploiting makeup performance quality in addition to the other performance qualities.

A kit or device according to the invention also allows the user to modify the intensity of the colour effect by adjusting the proportion of the coloured gelled phase to be mixed.

Thus, the kits and devices according to the invention are particularly advantageous insofar as they afford the user the possibility of adjusting at will, by means of the choice of the gelled phases representative of the two types of oily and aqueous architecture, the desired makeup performance qualities, while at the same time ensuring convenience and ease of use.

The present invention especially makes it possible to afford the user wider makeup range and also to give the makeup operation an appealing fun aspect. Moreover, the fact that the mixing of the phases may be performed at room temperature is of manifest interest as regards the convenience and thus gives satisfaction as regards the simplicity of use.

According to another of its aspects, a subject of the invention is also a process, especially a cosmetic process, for making up and/or caring for a keratin material, in particular the skin and/or the lips, comprising at least one step that consists in applying to the said keratin material a composition in accordance with the invention.

According to yet another of its aspects, the present invention relates to a process, especially a cosmetic process, for making up and/or caring for a keratin material, in particular the skin and/or the lips, comprising at least the application to the said material of a composition, in a particular a macroscopically homogeneous composition obtained by extemporaneous mixing, before application or at the time of application to the said keratin material, of at least one aqueous phase gelled with at least one polymeric gelling agent that is natural or of natural origin, and of at least one oily phase gelled with at least one lipophilic gelling agent chosen from particulate gelling agents, organopolysiloxane elastomers, semi-crystalline polymers and dextrin esters, and mixtures thereof.

Cosmetic Composition

Firstly, it is important to note that a composition according to the invention is different from an emulsion.

An emulsion generally consists of an oily liquid phase and an aqueous liquid phase. It is a dispersion of droplets of one of the two liquid phases in the other. The size of the droplets forming the dispersed phase of the emulsion is typically about a micrometer (0.1 to 100 µm). Furthermore, an emulsion requires the presence of a surfactant or of a silicone emulsifier to ensure its stability over time.

In contrast, a composition according to the invention consists of a macroscopically homogeneous mixture of two immiscible gelled phases. These two phases both have a gel-type texture. This texture is especially reflected visually by a consistent, creamy appearance.

The term "macroscopically homogeneous mixture" means a mixture in which each of the gelled phases cannot be individualized with the naked eye.

More precisely, in a composition according to the invention, the gelled aqueous phase and the gelled oily phase interpenetrate and thus form a stable and, consistent product. This consistency is achieved by mixing interpenetrated oily and aqueous gelled macrodomains. These interpenetrated macrodomains are not measurable objects. Thus, by microscope, the composition according to the invention is very different from an emulsion.

It cannot be characterized either as having a "sense", i.e. an O/W or W/O sense.

Thus, a composition according to the invention has a gel-type consistency. Furthermore, the stability of the composition is long-lasting without surfactant. Consequently, a cosmetic composition according to the invention does not require any surfactant or silicone emulsifier to ensure its stability over time.

It is known from the state of the art to observe the intimate nature of the mixture of the aqueous and oily gels in a gel-type composition, for example, by introducing a dye substance into either the oily or aqueous gel phases before forming the gel-type composition. On visual inspection, the dye is seen to be uniformly dispersed, even though the dye is present in only one of the oily gel or aqueous gel. Indeed, if two different dyes of different colours are introduced into the oily and aqueous phases, respectively, before forming the gel-type composition, both colours can be observed uniformly dispersed throughout the gel-type composition. This is in contrast to an emulsion wherein if a dye that is either water-soluble or oil-soluble is introduced into the aqueous or oily phases, respectively, before forming an emulsion, only the colour of the dye in the external phase will be observed (Remington: The Science and Practice of Pharmacy, 19th Edition (1995) Chapter 21, page 282).

It is also known to distinguish a gel-type composition from an emulsion by performing a "drop test". This test consists to demonstrate the bi-continous nature of a gel-type composition. Indeed, as mentioned above, the composition's consistency is achieved by interpenetrating oily and aqueous gelled domains. Therefore, the bi-continous nature of a gel-type composition can be highlighted by a simple test with respectively hydrophilic and hydrophobic solvents. This test consists to deposit, on the one hand, a droplet of a hydrophilic solvent on a first sample of the tested composition, and, on the other hand, a droplet of hydrophobic solvent on a second sample of the same tested composition, and to analyze the behavior of both droplets of solvents. In the case of an O/W emulsion, a droplet of hydrophilic solvent diffuses in the sample and a droplet of hydrophobic solvent remains at the sample surface. In the case of a W/O emulsion, a droplet of hydrophilic solvent remains at the sample surface and a droplet of hydrophobic solvent diffuses throughout sample. Finally, in the case of a gel-type composition (bi-continuous system), the hydrophilic and hydrophobic droplets diffuse in the entire sample.

In particular, in the case of the present invention, the test which will be privileged for distinguishing a gel-type composition from an emulsion consists in a dilution test. Indeed, in a gel-type composition, the gelled aqueous domains and gel oily domains interpenetrate and form a stable and consistent product, whose dilution behavior in water and oil is different of emulsion's behavior. Therefore, the dilution behavior of a gel-type composition (bi-continuous system) can be compared to emulsions.

More specifically, the dilution test consists to put 40 g of product plus 160 g of dilution solvent (water or oil) in a 30 ml plastic beaker. The dilution is performed under controlled agitation to avoid any phenomenon of emulsification. In particular, it is done using a planetary mixer: Speed Mixer™ DAC400FVZ. The Speed Mixer is set to 1500 rpm for 4 minutes. Finally, observation of resulting sample is made with a light microscope at a magnification of ×100 (×10× 10). It may be noticed that oils like Parleam® and Xiameter PMX-200 Silicone Fluid 5CS® from Dow Corning are convenient as dilution solvents.

In the case of a gel-type composition (bi-continuous system), when diluted either in oil or water, a heterogeneous aspect is always observed. When a gel-type composition (bi-continuous system) is diluted with water, one will observe lumps of oily gel in suspension and when a gel-type composition (bi-continuous system) is diluted with oil, one will observe lumps of aqueous gel in suspension.

On the contrary, upon dilution, emulsions display a different behavior. An O/W emulsion when it is diluted with an aqueous solvent will gradually thin up without presenting a heterogeneous and lumpy aspect. This same O/W emulsion when diluted with oil will present a heterogeneous appearance (lumps of O/W emulsion suspended in oil). A W/O emulsion when diluted with an aqueous solvent will present a heterogeneous appearance (lumps of W/O emulsion is suspended in the water). This same W/O emulsion when diluted with oil will gradually thin up without presenting a heterogeneous and lumpy aspect.

In general, the aqueous gelled phase and the oily gelled phase forming a composition according to the invention are present in a weight ratio ranging from 95/5 to 5/95. More preferentially, the aqueous phase and the oily phase are present in a weight ratio ranging from 30/70 to 80/20.

The ratio between the two gelled phases is adjusted according to the desired cosmetic properties.

Thus, in the case of a composition intended for making up the skin and especially the face, it is advantageous to favour an aqueous phase/oily phase weight ratio greater than 1, especially ranging from 60/40 to 90/10, preferably ranging from 60/40 to 80/20, preferably from 60/40 to 70/30, and more preferably to favour an aqueous phase/oily phase weight ratio of 60/40 or 70/30.

These preferred ratios are particularly advantageous for obtaining fresh and light compositions.

Advantageously, a composition according to the invention is in the form of a creamy gel with a minimum stress below which it does not flow unless it has been subjected to an external mechanical stress.

As emerges from the text hereinbelow, a composition according to the invention may have a minimum threshold stress of 1.5 Pa and in particular greater than 10 Pa.

It may also advantageously have a stiffness modulus $G^*$ at least equal to 400 Pa and preferably greater than 1000 Pa.

According to an advantageous embodiment variant, the gelled phases under consideration to form a composition according to the invention may have, respectively, a threshold stress of greater than 1.5 Pa and preferably greater than 10 Pa.

Characterization of the threshold stresses is performed by oscillating rheology measurements. A method is proposed in the examples section of the present text.

In general, the corresponding measurements are taken at 25° C. using a Haake RS600 imposed-stress rheometer equipped with a plate-plate measuring body (60 mm diameter) fitted with an anti-evaporation device (bell jar). For each measurement, the sample is placed delicately in position and the measurements start 5 minutes after placing the sample in the air gap (2 mm). The tested composition is then subjected to a stress ramp from $10^{-2}$ to $10^3$ Pa at a set frequency of 1 Hz.

A composition according to the invention may also have a certain elasticity. This elasticity may be characterized by a stiffness modulus $G^*$ which, under this minimum stress threshold, may be at least equal to 400 Pa and preferably greater than 1000 Pa. The value $G^*$ of a composition may be obtained by subjecting the composition under consideration to a stress ramp from $10^{-2}$ to $10^3$ Pa at a set frequency of 1 Hz.

Hydrophilic Gelling Agent

For the purposes of the present invention, the term "hydrophilic gelling agent" means a compound that is capable of gelling the aqueous phase of the compositions according to the invention.

The gelling agent is hydrophilic and is thus present in the aqueous phase of the composition.

The gelling agent may be water-soluble or water-dispersible.

As stated above, the aqueous phase of a composition according to the invention is gelled with at least one hydrophilic gelling agent chosen from polymeric gelling agents that are natural or of natural origin, and mixtures thereof.

For the purposes of the invention, the expression "of natural origin" is intended to denote polymeric gelling agents that are obtained by modification of natural polymeric gelling agents.

These gelling agents may be particulate or non-particulate.

More precisely, these gelling agents fall within the category of polysaccharides.

In general, polysaccharides may be divided into several categories.

Thus, polysaccharides that are suitable for use in the invention may be homopolysaccharides such as fructans, glucans, galactans and mannans or heteropolysaccharides such as hemicellulose.

Similarly, they may be linear polysaccharides such as pullulan or branched polysaccharides such as gum arabic and amylopectin, or mixed polysaccharides such as starch.

More particularly, the polysaccharides that are suitable for use in the invention may be distinguished according to whether or not they are starchy.

Starchy Polysaccharides

Representatives of this category that may most particularly be mentioned include native starches, modified starches and particulate starches.

Native Starches

The starches that may be used in the present invention are more particularly macromolecules in the form of polymers consisting of elemental units which are anhydroglucose (dextrose) units, linked via α(1,4) bonds, of chemical formula $(C_6H_{10}O_5)_n$. The number of these units and their assembly make it possible to distinguish amylose, which is a molecule formed from about 600 to 1000 linearly linked glucose molecules, and amylopectin, which is a polymer that is branched every 25 glucose residues approximately (α(1,6) bond). The total chain may contain between 10 000 and 100 000 glucose residues.

Starch is described in particular in Kirk-Othmer's *Encyclopaedia of Chemical Technology,* 3rd edition, volume 21, pages 492-507, Wiley Interscience, 1983.

The relative proportions of amylose and of amylopectin, and their degree of polymerization, vary as a function of the botanical origin of the starches. On average, a sample of native starch consists of about 25% amylose and 75% amylopectin.

Occasionally, phytoglycogen is present (between 0% and 20% of starch), this molecule being an analogue of amylopectin but branched every 10 to 15 glucose residues.

Starch may be in the form of semi-crystalline granules: amylopectin is organized in leaflets, amylose forms an amorphous zone that is less well organized between the various leaflets.

Amylose self-organizes in a right-handed helix with six glucoses per turn. It dissociates into glucose which may be assimilated under the action of enzymes, amylases, all the more readily if it is in the form of amylopectin. Specifically, the helix formation does not favour the accessibility of starch to enzymes.

Starches are generally in the form of a white powder, which is insoluble in cold water, whose elemental particle size ranges from 3 to 100 microns.

By treating it with hot water, starch paste is obtained. It is used in industry for its thickening and gelling properties.

The botanical origin of the starch molecules used in the present invention may be cereals or tubers. Thus, the starches are chosen, for example, from corn starch, rice starch, cassava starch, tapioca starch, barley starch, potato starch, wheat starch, sorghum starch and pea starch.

Native starches are represented, for example, by the products sold under the names C*Amilogel™, Cargill Gel™, C* Gel™, Cargill Gum™, DryGel™ and C*Pharm Gel™ by the company Cargill, under the name Amidon de maïs by the company Roquette, and under the name Pure Tapioca by the company National Starch.

Modified Starches

The modified starches used in the composition of the invention may be modified via one or more of the following reactions: pregelatinization, degradation (acid hydrolysis, oxidation or dextrinization), substitution (esterification or etherification), crosslinking (esterification), bleaching.

More particularly, these reactions may be performed in the following manner:

pregelatinization by splitting the starch granules (for example drying and cooking in a drying drum);

acid hydrolysis giving rise to very rapid retrogradation on cooling;

oxidation with strong oxidizing agents (alkaline medium, in the presence of sodium hypochlorite NaOCl, for example) leading to depolymerization of the starch molecule and to the introduction of carboxyl groups into the starch molecule (mainly oxidation of the $C_6$ hydroxyl group);

dextrinization in acidic medium at high temperature (hydrolysis followed by repolymerization);

crosslinking with functional agents capable of reacting with the hydroxyl groups of starch molecules which will thus be linked together (for example with glyceryl and/or phosphate groups);

esterification in alkaline medium for the grafting of functional groups, especially $C_1$-$C_6$ acyl (acetyl), $C_1$-$C_6$ hydroxyalkyl (hydroxyethyl or hydroxypropyl), carboxymethyl or octenylsuccinic.

Monostarch phosphates (of the type St-O—PO—(OX)$_2$), distarch phosphates (of the type St-O—PO—(OX)—O—St) or even tristarch phosphates (of the type St-O—PO—(O-St)$_2$) or mixtures thereof may especially be obtained by crosslinking with phosphorus compounds.

X especially denotes alkali metals (for example sodium or potassium), alkaline-earth metals (for example calcium or magnesium), ammonium salts, amine salts, for instance those of monoethanolamine, diethanolamine, triethanolamine, 3-amino-1,2-propanediol, or ammonium salts derived from basic amino acids such as lysine, arginine, sarcosine, ornithine or citrulline.

The phosphorus compounds may be, for example, sodium tripolyphosphate, sodium orthophosphate, phosphorus oxychloride or sodium trimetaphosphate.

According to the invention, it is also possible to use amphoteric starches, these amphoteric starches containing one or more anionic groups and one or more cationic groups. The anionic and cationic groups may be linked to the same reactive site of the starch molecule or to different reactive sites; they are preferably linked to the same reactive site. The anionic groups may be of carboxylic, phosphate or sulfate type, preferably carboxylic. The cationic groups may be of primary, secondary, tertiary or quaternary amine type.

The amphoteric starches are especially chosen from the compounds having the following formulae:

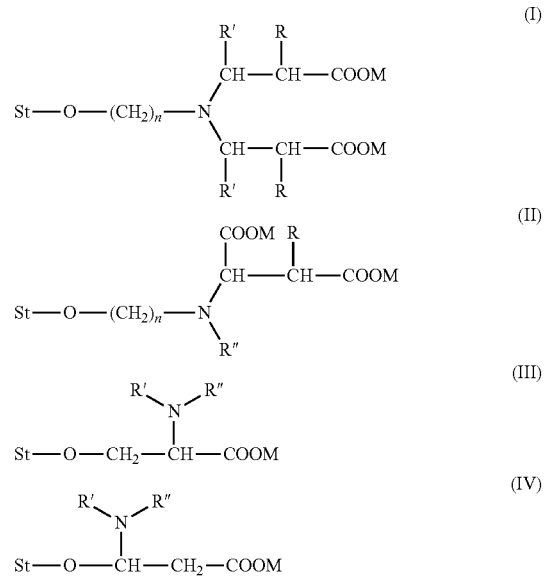

in which:

St-O represents a starch molecule;

R, which may be identical or different, represents a hydrogen atom or a methyl radical;

R', which may be identical or different, represents a hydrogen atom, a methyl radical or a —COOH group;

n is an integer equal to 2 or 3;

M, which may be identical or different, denotes a hydrogen atom, an alkali metal or alkaline-earth metal such as Na, K, Li or $NH_4$, a quaternary ammonium or an organic amine;

R" represents a hydrogen atom or an alkyl radical containing from 1 to 18 carbon atoms.

These compounds are especially described in U.S. Pat. Nos. 5,455,340 and 4,017,460.

The starch molecules may be derived from any plant source of starch, especially such as corn, potato, oat, rice, tapioca, sorghum, barley or wheat. It is also possible to use the hydrolysates of the starches mentioned above.

The modified starches are represented, for example, by the products sold under the names C*Tex-Instant (pregelatinized adipate), C*StabiTex-Instant (pregelatinized phosphate), C*PolarTex-Instant (pregelatinized hydroxypropyl), C*Set (acid hydrolysis, oxidation), C*size (oxidation), C*BatterCrisp (oxidation), C*DrySet (dextrinization), C*Tex™ (acetylated distarch adipate), C*PolarTex™ (hydroxypropyl distarch phosphate), C* StabiTex™ (distarch phosphate, acetylated distarch phosphate) by the company Cargill, by distarch phosphates or compounds that are rich in distarch phosphate, such as the product sold under the references Prejel VA-70-T AGGL (gelatinized hydroxypropyl cassava distarch phosphate) or Prejel TK1 (gelatinized cassava distarch phosphate) or Prejel 200 (gelatinized acetylated cassava distarch phosphate) by the company Avebe or Structure *Zea* from National Starch (gelatinized corn distarch phosphate).

As examples of oxidized starches, use will be made especially of those sold under the name C*size from the company Cargill.

The native or modified starches described above may advantageously be used in a proportion of from 0.1% to 8% by weight of solids and preferably about 1% by weight, relative to the total weight of the aqueous phase.

Particulate Starches

Particulate starches that may be mentioned in particular include:

- starches grafted with an acrylic polymer (homopolymer or copolymer) and in particular with sodium polyacrylate, for instance those sold under the name Sanfresh ST-100MC by the company Sanyo Chemical Industries or Makimousse 25 or Makimousse 12 by the company Daito Kasei (INCI name: Sodium polyacrylate starch);
- hydrolysed starches grafted with an acrylic polymer (homopolymer or copolymer) and especially acryloacrylamide/sodium acrylate copolymer, for instance those sold under the names Water Lock A-240, A-180, B-204, D-223, A-100, C-200 and D-223 by the company Grain Processing (INCI name: Starch/acrylamide/sodium acrylate copolymer);
- polymers based on starch, gum and cellulose derivative, such as the product containing starch and sodium carboxymethylcellulose, sold under the name Lysorb 220 by the company Lysac.

Mention may also be made most particularly of ($C_1$-$C_4$) carboxyalkyl starches, also referred to hereinbelow as "carboxyalkyl starch", which are obtained by grafting carboxyalkyl groups onto one or more alcohol functions of starch, especially by reaction of starch and of sodium monochloroacetate in alkaline medium.

The carboxyalkyl groups are generally attached via an ether function, more particularly to carbon 1. The degree of substitution with carboxyalkyl units of the ($C_1$-$C_4$) carboxyalkyl starch preferably ranges from 0.1 to 1 and more particularly from 0.15 to 0.5. The degree of substitution is defined according to the present invention as being the mean number of hydroxyl groups substituted with an ester or ether group per monosaccharide unit of the polysaccharide.

The carboxyalkyl starches are advantageously used in the form of salts and especially salts of alkali metals or alkaline-earth metals such as Na, K, Li, $NH_4$, or salts of a quaternary ammonium or of an organic amine such as monoethanolamine, diethanolamine or triethanolamine. The ($C_1$-$C_4$) carboxyalkyl starches are, in the context of the present invention, advantageously carboxymethyl starches. The carboxymethyl starches preferably comprise units having the following formula:

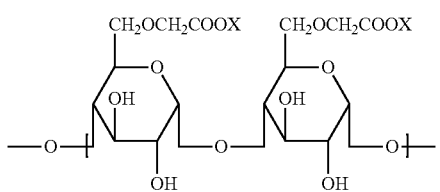

in which X, optionally covalently bonded to the carboxyl unit, denotes a hydrogen atom, an alkali metal or alkaline-earth metal such as Na, K, Li, $NH_4$, a quaternary ammonium or an organic amine, for instance monoethanolamine, diethanolamine or triethanolamine.

Preferably, X denotes an $Na^+$ cation. The carboxyalkyl starches that may be used according to the present invention are preferably non-pregelatinized carboxyalkyl starches. The carboxyalkyl starches that may be used according to the present invention are preferably partially or totally crosslinked carboxyalkyl starches.

In general, a crosslinked carboxyalkyl starch has, as opposed to a non-crosslinked carboxyalkyl starch, an increased, controllable viscosity and greater stability. The crosslinking thus makes it possible to reduce the syneresis and to increase the resistance of the gel to shear effects.

The carboxyalkyl starches under consideration according to the invention are more particularly potato carboxyalkyl starches. Thus, the carboxyalkyl starches that may be used according to the present invention are preferably sodium salts of carboxyalkyl starches, in particular a sodium salt of potato carboxymethyl starch, sold especially under the name Primojel® by the company DMV International or Glycolys® and Glycolys® LV by the company Roquette.

According to one particular embodiment, the potato carboxymethyl starches sold especially under the name Glycolys® by the company Roquette will be used. As stated previously, the ($C_1$-$C_4$) carboxyalkyl starch particles are present in the compositions according to the invention in a swollen and unsplit form. This swelling may be characterized by a swelling power Q that may advantageously be between 10 and 30 ml/g and preferably between 15 and 25 ml (volume of liquid absorbed)/g of dry particulate material.

Thus, the size of the swollen carboxyalkyl starch particles used according to the present invention generally ranges from 25 to 300 μm. For example, the gel Primojel® containing 10% by weight of potato carboxyalkyl starch and sodium salt in water contains more than 80% of swollen particles of this starch with a diameter of greater than 50 microns and more particularly greater than 100 microns.

According to a preferred embodiment variant of the invention, these particles are used for the preparation of the compositions according to the invention, in this swollen particulate state. To do this, these particles are advantageously used in the form of an aqueous gel that is either prepared beforehand or already commercially available. The gels under consideration according to the invention are advantageously translucent.

For example, a carboxymethyl starch gel such as Primojel® which is at a concentration of 10% by weight may be adjusted to the required concentration before being used to prepare the expected cosmetic composition.

Such a particulate starch may be used in a proportion of from 0.1% to 5% by weight of solids relative to the total weight of the aqueous phase, preferably between 0.5% and 2.5% by weight and in particular in a proportion of about 1.5% by weight, relative to the total weight of the aqueous phase.

Non-Starchy Polysaccharides

In general, the non-starchy polysaccharides may be chosen from polysaccharides produced by microorganisms; polysaccharides isolated from algae, and polysaccharides from higher plants, such as homogeneous polysaccharides, in particular celluloses and derivatives thereof or fructosans, heterogeneous polysaccharides such as gum arabics, galactomannans, glucomannans and pectins, and derivatives thereof.

In particular, the polysaccharides may be chosen from fructans, gellans, glucans, amylose, amylopectin, glycogen, pullulan, dextrans, celluloses and derivatives thereof, in particular methylcelluloses, hydroxyalkylcelluloses, ethylhydroxyethylcelluloses and carboxymethylcelluloses, mannans, xylans, lignins, arabans, galactans, galacturonans, alginate-based compounds, chitin, chitosans, glucuronoxylans, arabinoxylans, xyloglucans, glucomannans, pectic acids and pectins, arabinogalactans, carrageenans, agars, glycosaminoglycans, gum arabics, tragacanth gums, ghatti gums, karaya gums, locust bean gums, galactomannans such as guar gums and nonionic derivatives thereof, in particular hydroxypropyl guar, and ionic derivatives thereof, biopolysaccharide gums of microbial origin, in particular scleroglucan or xanthan gums, mucopolysaccharides, and in particular chondroitin sulfates, and mixtures thereof.

Advantageously, a composition according to the invention comprises as polymeric gelling agent that is natural or of natural origin at least one polysaccharide chosen from carrageenans, in particular kappa-carrageenans, gellan gum, agar-agar, xanthan gum, alginate-based compounds, in particular sodium alginate, scleroglucan gum, guar gum, inulin and pullulan, and mixtures thereof.

These polysaccharides may be chemically modified, especially with urea or urethane groups, or by a hydrolysis, oxidation, esterification, etherification, sulfatation, phosphatation, amination, amidation or alkylation reaction, or by several of these modifications.

The derivatives obtained may be anionic, cationic, amphoteric or nonionic.

Advantageously, the polysaccharides may be chosen from carrageenans, in particular kappa-carrageenans, gellan gum, agar-agar, xanthan gum, alginate-based compounds, in particular sodium alginate, scleroglucan gum, guar gum, inulin and pullulan, and mixtures thereof.

In general, the compounds of this type that may be used in the present invention are chosen from those described especially in Kirk-Othmer's *Encyclopedia of Chemical Technology*, Third Edition, 1982, volume 3, pp. 896-900, and volume 15, pp. 439-458, in *Polymers in Nature* by E. A. McGregor and C. T. Greenwood, published by John Wiley & Sons, Chapter 6, pp. 240-328, 1980, in the publication by Robert L. Davidson entitled *Handbook of Water-soluble Gums and Resins* published by McGraw-Hill Book Company (1980) and in *Industrial Gums—Polysaccharides and their Derivatives*, edited by Roy L. Whistler, Second Edition, published by Academic Press Inc.

Such a gelling agent may be used in a proportion of from 0.1% to 8% by weight of solids relative to the total weight of the aqueous phase, especially from 0.1% to 6% by weight, preferably between 0.5% and 2.5% by weight, in particular in a proportion of about 1% or even in a proportion of about 1.5% by weight, relative to the total weight of the aqueous phase.

More precisely, these polysaccharides that are suitable for use in the invention may be distinguished according to whether they are derived from microorganisms, algae or higher plants, and are detailed below.

Polysaccharides Produced by Microorganisms

Xanthan

Xanthan is a heteropolysaccharide produced on an industrial scale by the aerobic fermentation of the bacterium *Xanthomonas campestris*. Its structure is composed of a main chain of β-D-glucoses connected in β(1,4) manner, similar to cellulose. One glucose molecule out of two bears a trisaccharide side chain composed of an α-D-mannose, of a β-D-glucuronic acid and of a terminal β-D-mannose. The internal mannose residue is generally acetylated on carbon 6. Approximately 30% of the terminal mannose residues bear a pyruvate group linked in chelated form between carbons 4 and 6. The glucuronic acids and the charged pyruvic acids are ionizable and thus responsible for the anionic nature of xanthan (negative charge down to pH 1). The content of the pyruvate and acetate residues varies according to the bacterial strain, the fermentation process, the post-fermentation conditions and the purification stages. These groups can be neutralized in the commercial products with $Na^+$, $K^+$ or $Ca^{2+}$ ions (Satia, 1986). The neutralized form can be converted into the acid form by ion exchange or by dialysis with an acid solution.

Xanthan gums have a molecular weight of between 1 000 000 and 50 000 000 and a viscosity of between 0.6 and 1.65 Pa·s for an aqueous composition comprising 1% of xanthan gum (measured at 25° C. using a Brookfield viscometer, LVT type, at 60 revolutions per minute).

Xanthan gums are represented, for example, by the products sold under the name Rhodicare by the company Rhodia Chimie, under the name Satiaxane™ by the company Cargill Texturizing Solutions (for the food, cosmetic and pharmaceutical industry), under the name Novaxan™ by the company ADM and under the names Kelzan® and Keltrol® by the company CP-Kelco.

Pullulan

Pullulan is a polysaccharide consisting of maltotriose units, known under the name α(1,4)-α(1,6)-glucan. Three glucose units in maltotriose are connected via an α(1,4) glycosidic bond, whereas the consecutive maltotriose units are connected to each other via an α(1,6) glycosidic bond.

Pullulan is produced, for example, under the reference Pullulan PF 20 by the company Hayashibara in Japan.

Dextran and Dextran Sulfate

Dextran is a neutral polysaccharide not bearing any charge groups, which is biologically inert, prepared by fermentation of beet sugar containing only hydroxyl groups.

It is possible to obtain, from native dextran by hydrolysis and purification, dextran fractions of different molecular weights. Dextran may in particular be in the form of dextran sulfate.

Dextran is represented, for example, by the products sold under the name Dextran or Dextran T by the company Pharmacosmos, under the name Dextran 40 Powder or Dextran 70 Powder by the company Meito Sangyo Co. Dextran sulfate is sold by the company PK Chemical A/S under the name Dextran Sulfate.

Succinoglycan

Succinoglycan is an extracellular polymer produced by bacterial fermentation, of high molecular weight, consisting of octasaccharide repeating units (8 repeating sugars). Succinoglycans are sold, for example, under the name Rheozan by the company Rhodia.

Scleroglucan

Scleroglucan is a nonionic branched homopolysaccharide consisting of β-D glucan units. The molecules consist of a main linear chain formed by D-glucose units linked via β(1,3) bonds, and of which one in three units is linked to a D-glucose side unit via a β(1,6) bond.

A fuller description of scleroglucans and of their preparation may be found in document U.S. Pat. No. 3,301,848.

Scleroglucan is sold, for example, under the name Amigel by the company Alban Muller, or under the name Actigum™ CS by the company Cargill.

Gellan Gum

Gellan gum is an anionic linear heteropolysaccharide based on oligosaccharide units composed of 4 saccharides (tetrasaccharide). D-Glucose, L-rhamnose and D-glucuronic acid in 2/1/1 proportions are present in gellan gum in the form of monomer elements.

It is sold, for example, under the name Kelcogel CG LA by the company CP Kelco.

Polysaccharides Isolated from Algae

Galactans

The polysaccharide according to the invention may be a galactan chosen especially from agar and carrageenans.

Carrageenans are anionic polysaccharides constituting the cell walls of various red algae (Rhodophyceae) belonging to the Gigartinaceae, Hypneaceae, Furcellariaceae and Polyideaceae families. They are generally obtained by hot aqueous extraction from natural strains of the said algae. These linear polymers, formed by disaccharide units, are composed of two D-galactopyranose units alternately linked via α(1,3) and β(1,4) bonds. These are highly sulfated polysaccharides (20-50%) and the α-D-galactopyranosyl residues may be in 3,6-anhydro form. According to the number and position of the ester sulfate groups on the repeat disaccharide of the molecule, several types of carrageenan are distinguished, namely: kappa-carrageenans, which bear one ester sulfate group, iota-carrageenans which bear two ester sulfate groups, and lambda-carrageenans which bear three ester sulfate groups.

Carrageenans are composed essentially of potassium, sodium, magnesium, triethanolamine and/or calcium salts and of ester sulfates of polysaccharides.

Carrageenans are sold especially by the company SEPPIC under the name Solagum®, by the company Gelymar under the names Carragel®, Carralact® and Carrasol®, by the company Cargill under the names Satiagel™ and Satiagum™, and by the company CP-Kelco under the names Genulacta®, Genugel® and Genuvisco®.

Galactans of agar type are galactose polysaccharides contained in the cell wall of some of these species of red algae (Rhodophyceae). They are formed from a polymer group in which the base backbone is a β(1,3) D-galactopyranose and α(1,4) L 3-6 anhydrogalactose chain, these units repeating regularly and alternately. The differences within the agar family are due to the presence or absence of methyl or carboxyethyl solvated groups. These hybrid structures are generally present in variable percentage, depending on the species of algae and the season of harvest.

Agar-agar is a mixture of polysaccharides (agarose and agaropectin) of high molecular mass, between 40 000 and 300 000 g·mol$^{-1}$. It is obtained by manufacturing algal extraction juices, generally by autoclaving, and by treating these juices comprising about 2% agar-agar, in order to extract the latter.

Agar is produced, for example, by the group B&V Agar Producers under the names Gold Agar, Agarite and Grand Agar by the company Hispanagar, and under the names Agar-Agar, QSA (Quick Soluble Agar) and Puragar by the company Setexam.

Furcellaran

Furcellaran is obtained commercially from red algae *Furcellaria fasztigiata*. Furcellaran is produced, for example, by the company Est-Agar.

Alginate-Based Compound

For the purposes of the invention, the term "alginate-based compound" means alginic acid, alginic acid derivatives and the salts of alginic acid (alginates) or of the said derivatives.

Preferably, the alginate-based compound is water-soluble.

Alginic acid, a natural substance derived from brown algae or certain bacteria, is a polyuronic acid composed of two uronic acids linked by 1,4-glycosidic bonds: β-D-mannuronic (M) acid and α-L-glucuronic (G) acid.

Alginic acid is capable of forming water-soluble salts (alginates) with alkali metals such as sodium, potassium or lithium, substituted cations of lower amines and of ammonium such as methylamine, ethanolamine, diethanolamine or triethanolamine. These alginates are water-soluble in aqueous medium at a pH equal to 4 but dissociate into alginic acid at a pH below 4.

This (these) alginate-based compound(s) is/are capable of crosslinking in the presence of at least one crosslinking agent, by formation of ionic bonds between the said alginate-based compound(s) and the said crosslinking agent(s). The formation of multiple crosslinking between several molecules of the said alginate-based compound(s) leads to the formation of a water-insoluble gel.

Use is preferably made of alginate-based compounds with a weight-average molecular mass ranging from 10 000 to 1 000 000, preferably from 15 000 to 500 000 and better still from 20 000 to 250 000.

According to a preferred embodiment, the alginate-based compound is alginic acid and/or a salt thereof.

Advantageously, the alginate-based compound is an alginate salt, and preferably sodium alginate.

The alginate-based compound may be chemically modified, especially with urea or urethane groups, or by a hydrolysis, oxidation, esterification, etherification, sulfatation, phosphatation, amination, amidation or alkylation reaction, or by several of these modifications.

The derivatives obtained may be anionic, cationic, amphoteric or nonionic.

The alginate-based compound(s) that is/are suitable for use in the invention may be represented, for example, by the products sold under the names Kelcosol, Satialgine™, Cecalgum™ or Algogel™ by the company Cargill Products, under the name Protanal™ by the company FMC Biopolymer, under the name Grindsted® Alginate by the company Danisco, under the name Kimica Algin by the company Kimica, and under the names Manucol® and Manugel® by the company ISP.

Polysaccharides from Higher Plants

This category of polysaccharides may be divided into homogeneous polysaccharides (only one species of saccharide) and heterogeneous polysaccharides composed of several types of saccharide.

a) Homogeneous Polysaccharides and Derivatives Thereof

The polysaccharide according to the invention may be chosen from celluloses and derivatives or fructosans.

Celluloses and Derivatives

The polysaccharide according to the invention may also be a cellulose or a derivative thereof, especially cellulose ethers or esters (e.g.: methylcellulose, carboxymethylcellulose, hydroxymethylcellulose, hydroxyethylcellulose, hydroxypropylcellulose, hydroxymethylpropylcellulose, cellulose acetate, cellulose nitrate, nitrocellulose).

The invention may also contain a cellulose-based associative polymer. According to the invention, the term "cellulose-based compound" means any polysaccharide compound bearing in its structure linear sequences of anhydroglucopyranose (AGU) residues linked via β(1,4) glycosidic bonds. The repeating unit is the cellobiose dimer. AGUs are found in chair conformation and bear three hydroxyl functions: two secondary alcohols (in positions 2 and 3) and a primary alcohol (in position 6). The polymers thus formed combine together via intermolecular bonds of hydrogen bonding type, thus giving the cellulose a fibrillar structure (about 1500 molecules per fibre).

The degree of polymerization differs enormously according to the origin of the cellulose; its value may range from a few hundred to a few tens of thousands.

Cellulose has the following chemical structure:

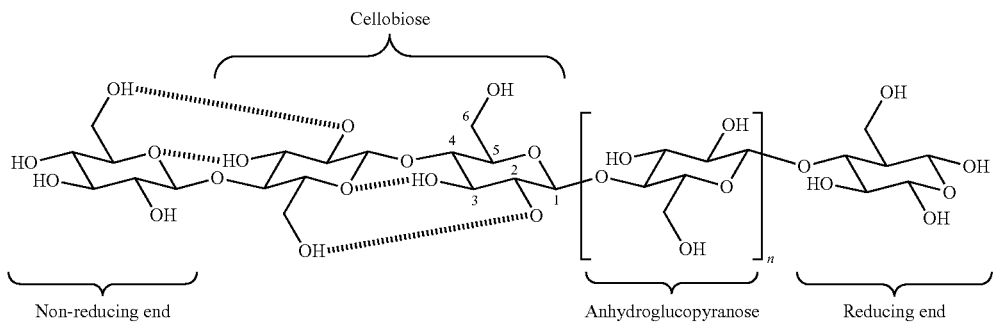

The hydroxyl groups of cellulose may react partially or totally with different chemical reagents to give cellulose derivatives having intrinsic properties. The cellulose derivatives may be anionic, cationic, amphoteric or nonionic. Among these derivatives, cellulose ethers, cellulose esters and cellulose ester ethers are distinguished.

Among the nonionic cellulose ethers, mention may be made of alkylcelluloses such as methylcelluloses and ethylcelluloses, hydroxyalkylcelluloses such as hydroxymethylcelluloses, hydroxyethylcelluloses and hydroxypropylcelluloses, and mixed hydroxyalkylalkylcelluloses such as hydroxypropylmethylcelluloses, hydroxyethylmethylcelluloses, hydroxyethylethylcelluloses and hydroxybutylmethylcelluloses.

Among the anionic cellulose ethers, mention may be made of carboxyalkylcelluloses and salts thereof. By way of example, mention may be made of carboxymethylcelluloses, carboxymethylmethylcelluloses and carboxymethylhydroxyethylcelluloses and sodium salts thereof.

Among the cationic cellulose ethers, mention may be made of crosslinked or non-crosslinked, quaternized hydroxyethylcelluloses.

The quaternizing agent may in particular be glycidyltrimethylammonium chloride or a fatty amine such as laurylamine or stearylamine. Another cationic cellulose ether that may be mentioned is hydroxyethylcellulosehydroxypropyltrimethylammonium.

The quaternized cellulose derivatives are, in particular:
quaternized celluloses modified with groups comprising at least one fatty chain, such as alkyl, arylalkyl or alkylaryl groups comprising at least 8 carbon atoms, or mixtures thereof
quaternized hydroxyethylcelluloses modified with groups comprising at least one fatty chain, such as alkyl, arylalkyl or alkylaryl groups comprising at least 8 carbon atoms, or mixtures thereof.

The alkyl radicals borne by the above quaternized celluloses or hydroxyethylcelluloses preferably comprise from 8 to 30 carbon atoms. The aryl radicals preferably denote phenyl, benzyl, naphthyl or anthryl groups.

Examples of quaternized alkylhydroxyethylcelluloses containing $C_8$-$C_{30}$ fatty chains that may be indicated include the products Quatrisoft LM 200, Quatrisoft LM-X 529-18-A, Quatrisoft LM-X 529-18B ($C_{12}$ alkyl) and Quatrisoft LM-X 529-8 ($C_{18}$ alkyl) sold by the company Amerchol, and the products Crodacel QM, Crodacel QL ($C_{12}$ alkyl) and Crodacel QS ($C_{18}$ alkyl) sold by the company Croda.

Among the cellulose derivatives, mention may also be made of:
celluloses modified with groups comprising at least one fatty chain, for instance hydroxyethylcelluloses modified with groups comprising at least one fatty chain, such as alkyl groups, especially of $C_8$-$C_{22}$, arylalkyl and alkylaryl groups, such as Natrosol Plus Grade 330 CS ($C_{16}$ alkyls) sold by the company Aqualon, and
celluloses modified with alkylphenyl polyalkylene glycol ether groups, such as the product Amercell Polymer HM-1500 (nonylphenyl polyethylene glycol (15) ether) sold by the company Amerchol.

Among the cellulose esters are mineral esters of cellulose (cellulose nitrates, sulfates, phosphates, etc.), organic esters of cellulose (cellulose monoacetates, triacetates, amidopropionates, acetatebutyrates, acetatepropionates, acetatetrimellitates, etc.), and mixed organic/mineral esters of cellulose, such as cellulose acetatebutyrate sulfates and cellulose acetatepropionate sulfates. Among the cellulose ester ethers, mention may be made of hydroxypropylmethylcellulose phthalates and ethylcellulose sulfates.

The cellulose-based compounds of the invention may be chosen from unsubstituted celluloses and substituted celluloses.

The celluloses and derivatives are represented, for example, by the products sold under the names Avicel® (microcrystalline cellulose, MCC) by the company FMC Biopolymers, under the name Cekol (carboxymethylcellulose) by the company Noviant (CP-Kelco), under the name Akucell AF (sodium carboxymethylcellulose) by the company Akzo Nobel, under the name Methocel™ (cellulose ethers) and Ethocel™ (ethylcellulose) by the company Dow, and under the names Aqualon (carboxymethylcellulose and sodium carboxymethylcellulose), Benecel® (methylcellulose), Blanose™ (carboxymethylcellulose), Culminal® (methylcellulose, hydroxypropylmethylcellulose), Klucel® (hydroxypropylcellulose), Polysurf® (cetylhydroxyethylcellulose) and Natrosol® CS (hydroxyethylcellulose) by the company Hercules Aqualon.

Fructosans

The polysaccharide according to the invention may especially be a fructosan chosen from inulin and derivatives thereof (especially dicarboxy and carboxymethyl inulins).

Fructans or fructosans are oligosaccharides or polysaccharides comprising a sequence of anhydrofructose units optionally combined with several saccharide residues other than fructose. Fructans may be linear or branched. Fructans may be products obtained directly from a vegetable or microbial source or alternatively products whose chain length has been modified (increased or decreased) by fractionation, synthesis or hydrolysis, in particular enzymatic. Fructans generally have a degree of polymerization from 2 to about 1000 and preferably from 2 to about 60.

Three groups of fructans are distinguished. The first group corresponds to products whose fructose units are for the most part linked via β(2,1) bonds. These are essentially linear fructans such as inulins.

The second group also corresponds to linear fructoses, but the fructose units are essentially linked via β(2,6) bonds. These products are levans.

The third group corresponds to mixed fructans, i.e. fructans containing β(2,6) and β(2,1) sequences. These are essentially branched fructans, such as graminans.

The fructans preferred in the compositions according to the invention are inulins. Inulin may be obtained, for example, from chicory, dahlia or Jerusalem artichoke, preferably from chicory.

In particular, the polysaccharide, especially the inulin, has a degree of polymerization from 2 to about 1000 and preferably from 2 to about 60, and a degree of substitution of less than 2 on the basis of one fructose unit.

The inulin used for this invention is represented, for example, by the products sold under the name Beneo™ Inulin by the company Orafti, and under the name Frutafit® by the company Sensus.

b) Heterogeneous Polysaccharides and Derivatives Thereof

Polysaccharides that may be used according to the invention may be gums, for instance *cassia* gum, karaya gum, konjac gum, gum tragacanth, tara gum, *acacia* gum or gum arabic.

Gum Arabic

Gum arabic is a highly branched acidic polysaccharide which is present in the form of mixtures of potassium, magnesium and calcium salts. The monomer elements of the free acid (arabic acid) are D-galactose, L-arabinose, L-rhamnose and D-glucuronic acid.

Galactomannans (guar, locust bean, fenugreek, tara gum) and derivatives (phosphated guar, hydroxypropyl guar, etc.)

Galactomannans are nonionic polysaccharides extracted from the albumin of seeds of leguminous plants, of which they constitute the storage carbohydrate. Galactomannans are macromolecules consisting of a main chain of D-mannopyranose units connected in β(1,4) fashion, carrying side branches consisting of a single D-galactopyranose unit connected in α(1,6) fashion to the main chain. The various galactomannans differ, on the one hand, in the proportion of α-D-galactopyranose units present in the polymer and, on the other hand, in significant differences in terms of distribution of the galactose units along the mannose chain.

The mannose/galactose (M/G) ratio is of the order of 2 for guar gum, of 3 for tara gum and of 4 for locust bean gum.

Galactomannans have the following chemical structure:

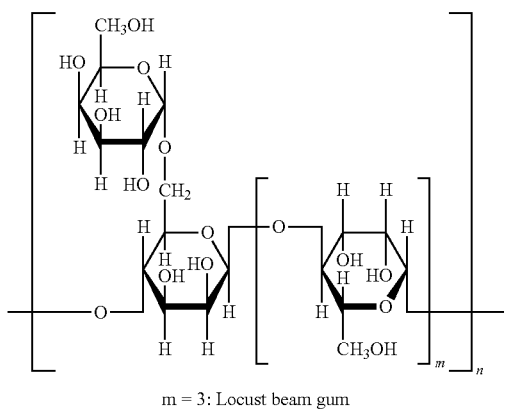

m = 3: Locust beam gum
m = 1: Guar gum
m = 2: Tara gum

Guar

Guar gum is characterized by a mannose:galactose ratio of the order of 2:1. The galactose group is uniformly distributed along the mannose chain.

The guar gums that may be used according to the invention may be nonionic, cationic or anionic. According to the invention, use may be made of unmodified or chemically modified nonionic guar gums.

Unmodified nonionic guar gums are, for example, the products sold under the names Vidogum GH, Vidogum G and Vidocrem by the company Unipektin and under the name Jaguar by the company Rhodia, under the name Meypro® Guar by the company Danisco, under the name Viscogum™ by the company Cargill and under the name Supercol® Guar Gum by the company Aqualon.

The hydrolysed nonionic guar gums that may be used according to the invention are represented, for example, by the products sold under the name Meyprodor® by the company Danisco.

The modified nonionic guar gums that may be used according to the invention are preferably modified with $C_1$-$C_6$ hydroxyalkyl groups, among which mention may be made, for example, of hydroxymethyl, hydroxyethyl, hydroxypropyl and hydroxybutyl groups.

Such nonionic guar gums optionally modified by hydroxyalkyl groups are sold, for example, under the trade names Jaguar HP 60, Jaguar HP 105 and Jaguar HP 120 (hydroxypropyl guar) by the company Rhodia or under the name N-Hance® HP (hydroxypropyl guar) by the company Aqualon.

The cationic galactomannan gums preferably have a cationic charge density of less than or equal to 1.5 meq/g and more particularly of between 0.1 and 1 meq/g. The charge density can be determined according to the Kjeldahl method. It generally corresponds to a pH of the order of 3 to 9.

Generally, for the purposes of the present invention, the term "cationic galactomannan gum" means any galactomannan gum containing cationic groups and/or groups that can be ionized into cationic groups.

The preferred cationic groups are chosen from those comprising primary, secondary, tertiary and/or quaternary amine groups.

The cationic galactomannan gums used generally have a weight-average molecular mass of between 500 and $5 \times 10^6$ approximately and preferably of between $10^3$ and $3 \times 10^6$ approximately.

The cationic galactomannan gums that may be used according to the present invention are, for example, gums comprising tri($C_1$-$C_4$)alkylammonium cationic groups. Preferably, 2% to 30% by number of the hydroxyl functions of these gums bear trialkylammonium cationic groups.

Mention may very particularly be made, among these trialkylammonium groups, of the trimethylammonium and triethylammonium groups.

Even more preferentially, these groups represent from 5% to 20% by weight relative to the total weight of the modified galactomannan gum.

According to the invention, the cationic galactomannan gum is preferably a guar gum comprising hydroxypropyltrimethylammonium groups, i.e. a guar gum modified, for example, with 2,3-epoxypropyltrimethylammonium chloride.

These galactomannan gums, in particular guar gums modified by cationic groups, are products already known per se and are, for example, described in the U.S. Pat. Nos. 3,589,578 and 4,031,307. Such products are furthermore sold in particular under the trade names of Jaguar Excel, Jaguar C13 S, Jaguar C 15, Jaguar C 17 and Jaguar C162 (Guar Hydroxypropyltrimonium Chloride) by the company Rhodia, under the name Amilan® Guar (Guar Hydroxypropyltrimonium Chloride) by the company Degussa and under the name N-Hance® 3000 (Guar Hydroxypropyltrimonium Chloride) by the company Aqualon.

The anionic guar gums that may be used according to the invention are polymers comprising groups derived from carboxylic acid, sulfonic acid, sulfenic acid, phosphoric acid, phosphonic acid or pyruvic acid. Preferably, the anionic group is a carboxylic acid group. The anionic group may also be in the form of an acid salt, especially a sodium, calcium, lithium or potassium salt.

The anionic guar gums that may be used according to the invention are preferentially carboxymethyl guar derivatives (carboxymethyl guar or carboxymethyl hydroxypropyl guar).

Locust Bean

Locust bean gum is extracted from the seeds of the carob tree (*Ceratonia siliqua*).

The unmodified locust bean gum that may be used in this invention is sold, for example, under the name Viscogum™ by the company Cargill, under the name Vidogum L by the company Unipektin or under the name Grinsted® LBG by the company Danisco.

The chemically modified locust bean gums that may be used in this invention may be represented, for example, by the cationic locust beans sold under the name Catinal CLB (Locust Bean Hydroxypropyltrimonium Chloride) by the company Toho.

Tara Gum

The tara gum that may be used in the context of this invention is sold, for example, under the name Vidogum SP by Unipektin.

Glucomannans (Konjac Gum)

Glucomannan is a polysaccharide of high molecular weight (500 000<Mglucomannan<2 000 000), composed of D-mannose and D-glucose units with a branch approximately every 50 or 60 units. It is found in wood but it is also the main constituent of konjac gum. Konjac (*Amorphophallus konjac*) is a plant of the Araceae family.

The products that may be used according to the invention are sold, for example, under the names Propol® and Rheolex® by the company Shimizu.

LM and HM Pectins and Derivatives

Pectins are linear polymers of α-D-galacturonic acid (at least 65%) linked in positions 1 and 4, with a certain proportion of carboxylic groups esterified with a methanol group. About 20% of the sugars constituting the pectin molecule are neutral sugars (L-rhamnose, D-glucose, D-galactose, L-arabinose, D-xylose). The L-rhamnose residues are present in all pectins, integrated into the main chain in positions 1,2.

The uronic acid molecules bear carboxyl functions. This function gives the pectins the capacity for exchanging ions, when they are in COO$^-$ form. Bivalent ions (in particular calcium) have the capacity of forming ionic bridges between two carboxyl groups of two different pectin molecules.

In the natural state, a certain proportion of the carboxylic groups are esterified with a methanol group. The natural degree of esterification of a pectin may range between 70% (apple, lemon) and 10% (strawberry) according to the source used. Starting with pectins with a high degree of esterification, it is possible to hydrolyse the —COOCH$_3$ group, so as to obtain weakly esterified pectins. Depending on the proportion of methylated or non-methylated monomers, the chain is therefore more or less acidic. Pectins are thus defined as being HM (high-methoxy) pectins, having a degree of esterification of greater than 50%, and LM (low-methoxy) pectins, having a degree of esterification of less than 50%.

In the case of amide pectins, the —OCH$_3$ group is substituted with a —NH$_2$ group. Pectins are especially sold by the company Cargill under the name Unipectine™, by the company CP-Kelco under the name Genu, and by Danisco under the name Grinsted Pectin.

Other Polysaccharides

Among the other polysaccharides that may be used according to the invention, mention may also be made of chitin (poly-N-acetyl-D-glucosamine, β(1,4)-2-acetamido-2-deoxy-D-glucose), chitosan and derivatives (chitosan β-glycerophosphate, carboxymethylchitin, etc.) such as those sold by the company France-Chitine; glycosaminoglycans (GAG) such as hyaluronic acid, chondroitin sulfate, dermatan sulfate and keratan sulfate, and preferably hyaluronic acid; xylans (or arabinoxylans) and derivatives.

Arabinoxylans are polymers of xylose and arabinose, which are grouped together under the name "pentosans".

Xylans consist of a main chain of D-xylose units linked in β(1,4) manner, and on which are found three substituents (Rouau & Thibault, 1987): acid units, α-L-arabinofuranose units, side chains which may contain arabinose, xylose, galactose and glucuronic acid.

According to this variant, the polysaccharide is preferably hyaluronic acid, or a salt thereof such as the sodium salt (sodium hyaluronate).

Lipophilic Gelling Agent

For the purposes of the present invention, the term "lipophilic gelling agent" means a compound that is capable of gelling the oily phase of the compositions according to the invention.

The gelling agent is lipophilic and is thus present in the oily phase of the composition.

The gelling agent is liposoluble or lipodispersible.

As emerges from the foregoing, the lipophilic gelling agent is advantageously chosen from particulate gelling agents, organopolysiloxane elastomers, semi-crystalline polymers and dextrin esters, and mixtures thereof.

I. Particulate Gelling Agents

The particulate gelling agent used in the composition according to the invention is in the form of particles, preferably spherical particles.

As representative lipophilic particulate gelling agents that are suitable for use in the invention, mention may be made most particularly of polar and apolar waxes, modified clays, and silicas such as fumed silicas and hydrophobic silica aerogels.

Waxes

The choice of a wax as lipophilic gelling agent is particularly advantageous for giving a composition according to the invention good emollience and comfort properties. Its combination with an aqueous phase gelled with a compound such as synthetic polymers gives access to compositions that have emollience and comfort with a fresh effect and advantageously an attenuated greasy feel. Compositions of this type are more particularly advantageous for dry to normal skin types.

The term "wax" under consideration in the context of the present invention generally means a lipophilic compound that is solid at room temperature (25° C.), with a solid/liquid reversible change of state, having a melting point of greater than or equal to 30° C., which may be up to 200° C. and in particular up to 120° C.

For the purposes of the invention, the melting point corresponds to the temperature of the most endothermic peak observed on thermal analysis (DSC) as described in standard ISO 11357-3; 1999. The melting point of the wax can be measured using a differential scanning calorimeter (DSC), for example the calorimeter sold under the name MDSC 2920 by the company TA Instruments.

The measurement protocol is as follows:

A 5 mg sample of wax placed in a crucible is subjected to a first temperature rise ranging from −20° C. to 100° C., at a heating rate of 10° C./minute, it is then cooled from 100° C. to −20° C. at a cooling rate of 10° C./minute and is finally subjected to a second temperature increase ranging from −20° C. to 100° C. at a heating rate of 5° C./minute. During the second temperature increase, the variation in the difference in power absorbed by the empty crucible and by the crucible containing the sample of wax is measured as a function of the temperature. The melting point of the compound is the temperature value corresponding to the top of the peak of the curve representing the variation in the difference in power absorbed as a function of the temperature.

The waxes that may be used in the compositions according to the invention are chosen from waxes that are solid at room temperature of animal, plant, mineral or synthetic origin, and mixtures thereof.

For the purposes of the invention, the waxes may be those generally used in cosmetics or dermatology. They may especially be polar or apolar, and hydrocarbon-based, silicone and/or fluoro waxes, optionally comprising ester or hydroxyl functions. They may also be of natural or synthetic origin.

a) Apolar Waxes

For the purposes of the present invention, the term "apolar wax" means a wax whose solubility parameter at 25° C. as defined below, $\delta_a$, is equal to 0 $(J/cm^3)^{1/2}$.

The definition and calculation of the solubility parameters in the Hansen three-dimensional solubility space are described in the paper by C. M. Hansen: "*The three-dimensional solubility parameters*", J. Paint Technol., 39, 105 (1967).

According to this Hansen space:

$\delta_D$ characterizes the London dispersion forces derived from the formation of dipoles induced during molecular impacts;

$\delta_p$ characterizes the Debye interaction forces between permanent dipoles and also the Keesom interaction forces between induced dipoles and permanent dipoles;

$\delta_h$ characterizes the specific interaction forces (such as hydrogen bonding, acid/base, donor/acceptor, etc.); and $\delta_a$ is determined by the equation: $\delta_a = (\delta_p^2 + \delta_h^2)^{1/2}$.

The parameters $\delta_p$, $\delta_h$, $\delta_D$ and $\delta_a$ are expressed in $(J/cm^3)^{1/2}$.

Apolar waxes are in particular hydrocarbon waxes consisting solely of carbon and hydrogen atoms and devoid of heteroatoms, such as N, O, Si and P.

The apolar waxes are chosen from microcrystalline waxes, paraffin waxes, ozokerite and polyethylene waxes, and mixtures thereof.

Mention may be made, as ozokerite, of Ozokerite Wax SP 1020 P.

As microcrystalline waxes that may be used, mention may be made of Multiwax W 445® sold by the company Sonneborn, Microwax HW® and Base Wax 30540® sold by the company Paramelt, and Cerewax® No. 3 sold by the company Baerlocher.

As microwaxes that may be used in the compositions according to the invention as apolar wax, mention may be made especially of polyethylene microwaxes such as those sold under the names Micropoly 200®, 220®, 220L® and 250S® by the company Micro Powders.

Polyethylene waxes that may be mentioned include Performalene 500-L Polyethylene and Performalene 400 Polyethylene sold by New Phase Technologies, and Asensa® SC 211 sold by the company Honeywell.

b) Polar Wax

For the purposes of the present invention, the term "polar wax" means a wax whose solubility parameter at 25° C., δa, is other than 0 $(J/cm^3)^{1/2}$.

In particular, the term "polar wax" means a wax whose chemical structure is formed essentially from, or even constituted of, carbon and hydrogen atoms, and comprising at least one highly electronegative heteroatom such as an oxygen, nitrogen, silicon or phosphorus atom.

The polar waxes may especially be hydrocarbon-based, fluoro or silicone waxes.

Preferentially, the polar waxes may be hydrocarbon-based waxes.

The term "hydrocarbon-based wax" means a wax formed essentially from, or even constituted of, carbon and hydrogen atoms, and optionally oxygen and nitrogen atoms, and not containing any silicon or fluorine atoms. It may contain alcohol, ester, ether, carboxylic acid, amine and/or amide groups.

According to the invention, the term "ester wax" means a wax comprising at least one ester function. According to the invention, the term "alcohol wax" means a wax comprising at least one alcohol function, i.e. comprising at least one free hydroxyl (OH) group.

The following may especially be used as ester wax: ester waxes such as those chosen from:

i) waxes of formula $R_1COOR_2$ in which $R_1$ and $R_2$ represent linear, branched or cyclic aliphatic chains in which the number of atoms ranges from 10 to 50, which may contain a heteroatom such as O, N or P and whose melting point ranges from 25 to 120° C.;

ii) bis(1,1,1-trimethylolpropane) tetrastearate, sold under the name Hest 2T-4S® by the company Heterene;

iii) diester waxes of a dicarboxylic acid of general formula $R^3$—(—OCO—$R^4$—COO—$R^5$), in which $R^3$ and $R^5$ are identical or different, preferably identical and represent a $C_4$-$C_{30}$ alkyl group (alkyl group comprising from 4 to 30 carbon atoms) and $R^4$ represents a linear or branched $C_4$-$C_{30}$ aliphatic group (alkyl group comprising from 4 to 30 carbon atoms) which may or may not contain one or more unsaturated groups, and preferably that is linear and unsaturated;

iv) mention may also be made of the waxes obtained by catalytic hydrogenation of animal or plant oils having linear or branched $C_8$-$C_{32}$ fatty chains, for example such as hydrogenated jojoba oil, hydrogenated sunflower oil, hydrogenated castor oil, hydrogenated coconut oil, and also the waxes obtained by hydrogenation of castor oil esterified with cetyl alcohol;

v) beeswax, synthetic beeswax, polyglycerolated beeswax, carnauba wax, candelilla wax, oxypropylenated lanolin wax, rice bran wax, ouricury wax, esparto grass wax, cork fibre wax, sugar cane wax, Japan wax, sumach wax, montan wax, orange wax, laurel wax, hydrogenated jojoba wax, sunflower wax, lemon wax, olive wax or berry wax.

According to another embodiment, the polar wax can be an alcohol wax. According to the invention, the term "alcohol wax" means a wax comprising at least one alcohol function, i.e. comprising at least one free hydroxyl (OH)

group. Examples of alcohol waxes that may be mentioned include the wax C30-50 Alcohols Performacol® 550 Alcohol sold by the company New Phase Technologies, stearyl alcohol and cetyl alcohol.

It is also possible to use silicone waxes, which may advantageously be substituted polysiloxanes, preferably of low melting point.

The term "silicone wax" means a wax comprising at least one silicon atom, and especially comprising Si—O groups.

Among the commercial silicone waxes of this type, mention may be made especially of those sold under the names Abilwax 9800, 9801 or 9810 (Goldschmidt), KF910 and KF7002 (Shin-Etsu), or 176-1118-3 and 176-11481 (General Electric).

The silicone waxes that may be used may also be alkyl or alkoxy dimethicones, and also ($C_{20}$-$C_{60}$)alkyl dimethicones, in particular ($C_{30}$-$C_{45}$)alkyl dimethicones, such as the silicone wax sold under the name SF-1642 by the company GE-Bayer Silicones or C30-45 alkyl dimethylsilyl polypropylsilsesquioxane sold under the name SW-8005® C30 Resin Wax by the company Dow Corning.

In the context of the present invention, particularly advantageous waxes that may be mentioned include polyethylene waxes, jojoba wax, candelilla wax and silicone waxes, in particular candelilla wax.

They may be present in the oily phase in a proportion of from 0.5% to 30% by weight relative to the weight of the oily phase, for example between 5% and 20% of the oily phase and more particularly from 2% to 15% by weight relative to the weight of the oily phase.

Modified Clays

The composition according to the invention may comprise at least one lipophilic clay.

The clays may be natural or synthetic, and they are made lipophilic by treatment with an alkylammonium salt such as a $C_{10}$ to $C_{22}$ ammonium chloride, for example distearyldimethylammonium chloride.

They may be chosen from bentonites, in particular hectorites and montmorillonites, beidellites, saponites, nontronites, sepiolites, biotites, attapulgites, vermiculites and zeolites.

They are preferably chosen from hectorites.

Hectorites modified with a $C_{10}$ to $C_{22}$ ammonium chloride, for instance hectorite modified with distearyldimethylammonium chloride, for instance the product sold under the name Bentone 38V® by the company Elementis or bentone gel in isododecane sold under the name Bentone Gel ISD V® (87% isododecane/10% disteardimonium hectorite/3% propylene carbonate) by the company Elementis, are preferably used as lipophilic clays.

Lipophilic clay may especially be present in a content ranging from 0.1% to 15% by weight, in particular from 0.5% to 10% and more particularly from 1% to 10% by weight relative to the total weight of the oily phase.

Silicas

The oily phase of a composition according to the invention may also comprise, as gelling agent, a fumed silica or silica aerogel particles.

a) Fumed Silica

Fumed silica which has undergone a hydrophobic surface treatment is most particularly suitable for use in the invention. Specifically, it is possible to chemically modify the surface of silica, by chemical reaction generating a reduced number of silanol groups present at the surface of the silica. Silanol groups can in particular be replaced by hydrophobic groups: a hydrophobic silica is then obtained.

The hydrophobic groups may be:

trimethylsiloxyl groups, which are obtained in particular by treating fumed silica in the presence of hexamethyldisilazane. Silicas thus treated are known as "silica silylate" according to the CTFA (8th edition, 2000). They are sold, for example, under the references Aerosil R812® by the company Degussa, and Cab-O-Sil TS-530® by the company Cabot;

dimethylsilyloxyl or polydimethylsiloxane groups, which are obtained in particular by treating fumed silica in the presence of polydimethylsiloxane or dimethyldichlorosilane. Silicas thus treated are named "Silica dimethyl silylate" according to the CTFA (8th edition, 2000). They are, for example, sold under the references Aerosil R972® and Aerosil R974® by the company Degussa and Cab-O-Sil TS-610® and Cab-O-Sil TS-720® by the company Cabot.

The fumed silicas may be present in a composition according to the present invention in a content of between 0.1% and 40% by weight, more particularly between 1% and 15% by weight and even more particularly between 2% and 10% by weight relative to the total weight of the oily phase.

b) Hydrophobic Silica Aerogels

The oily phase of a composition according to the invention may also comprise, as gelling agent, at least silica aerogel particles.

Silica aerogels are porous materials obtained by replacing (by drying) the liquid component of a silica gel with air.

They are generally synthesized via a sol-gel process in a liquid medium and then dried, usually by extraction with a supercritical fluid, the one most commonly used being supercritical $CO_2$. This type of drying makes it possible to avoid the contraction of the pores and of the material. The sol-gel process and the various drying operations are described in detail in Brinker C. J. and Scherer G. W., Sol-Gel Science, New York: Academic Press, 1990.

The hydrophobic silica aerogel particles used in the present invention have a specific surface area per unit of mass (SM) ranging from 500 to 1500 m$^2$/g, preferably from 600 to 1200 m$^2$/g and better still from 600 to 800 m$^2$/g, and a size expressed as the volume-mean diameter (D[0.5]) ranging from 1 to 1500 µm, better still from 1 to 1000 µm, preferably from 1 to 100 µm, in particular from 1 to 30 µm, more preferably from 5 to 25 µm, better still from 5 to 20 µm and even better still from 5 to 15 µm.

According to one embodiment, the hydrophobic silica aerogel particles used in the present invention have a size expressed as the volume-mean diameter (D[0.5]) ranging from 1 to 30 µm, preferably from 5 to 25 µm, better still from 5 to 20 µm and even better still from 5 to 15 µm.

The specific surface area per unit of mass can be determined by the nitrogen adsorption method, known as the BET (Brunauer-Emmett-Teller) method, described in the Journal of the American Chemical Society, Vol. 60, page 309, February 1938, which corresponds to international standard ISO 5794/1 (appendix D). The BET specific surface area corresponds to the total specific surface area of the particles under consideration.

The sizes of the silica aerogel particles can be measured by static light scattering using a commercial particle size analyser of MasterSizer 2000 type from Malvern. The data are processed on the basis of the Mie scattering theory. This theory, which is exact for isotropic particles, makes it possible to determine, in the case of nonspherical particles, an "effective" particle diameter. This theory is in particular described in the publication by Van de Hulst, H. C., "Light Scattering by Small Particles", Chapters 9 and 10, Wiley, New York, 1957.

According to an advantageous embodiment, the hydrophobic silica aerogel particles used in the present invention have a specific surface area per unit of mass (SM) ranging from 600 to 800 m$^2$/g.

The silica aerogel particles used in the present invention may advantageously have a tapped density ρ ranging from 0.02 g/cm$^3$ to 0.10 g/cm$^3$, preferably from 0.03 g/cm$^3$ to 0.08 g/cm$^3$ and in particular ranging from 0.05 g/cm$^3$ to 0.08 g/cm$^3$.

In the context of the present invention, this density may be assessed according to the following protocol, known as the tapped density protocol:

40 g of powder are poured into a measuring cylinder; the measuring cylinder is then placed on a Stay 2003 machine from Stampf Volumeter; the measuring cylinder is then subjected to a series of 2500 tapping actions (this operation is repeated until the difference in volume between two consecutive tests is less than 2%); the final volume Vf of tapped powder is then measured directly on the measuring cylinder. The tapped density is determined by the ratio m/Vf, in this instance 40/Vf (Vf being expressed in cm$^3$ and m in g).

According to one preferred embodiment, the hydrophobic silica aerogel particles used in the present invention have a specific surface area per unit of volume SV ranging from 5 to 60 m$^2$/cm$^3$, preferably from 10 to 50 m$^2$/cm$^3$ and better still from 15 to 40 m$^2$/cm$^3$.

The specific surface area per unit of volume is given by the relationship: $S_V = S_M \times \rho$; where ρ is the tapped density, expressed in g/cm$^3$, and SM is the specific surface area per unit of mass, expressed in m$^2$/g, as defined above.

Preferably, the hydrophobic silica aerogel particles according to the invention have an oil-absorbing capacity, measured at the wet point, ranging from 5 to 18 ml/g, preferably from 6 to 15 ml/g and better still from 8 to 12 ml/g.

The absorption capacity measured at the wet point, denoted Wp, corresponds to the amount of oil which it is necessary to add to 100 g of particles in order to obtain a homogeneous paste.

It is measured according to the "wet point" method or method for determining the oil uptake of a powder described in standard NF T 30-022. It corresponds to the amount of oil adsorbed onto the available surface of the powder and/or absorbed by the powder by measuring the wet point, described below:

an amount m=2 g of powder is placed on a glass plate, and the oil (isononyl isononanoate) is then added dropwise. After addition of 4 to 5 drops of oil to the powder, mixing is performed using a spatula, and addition of oil is continued until conglomerates of oil and powder have formed. From this point, the oil is added at a rate of one drop at a time and the mixture is subsequently triturated with the spatula. The addition of oil is stopped when a firm and smooth paste is obtained. This paste must be able to be spread over the glass plate without cracks or the formation of lumps. The volume Vs (expressed in ml) of oil used is then noted.

The oil uptake corresponds to the ratio Vs/m.

The aerogels used according to the present invention are aerogels of hydrophobic silica, preferably of silylated silica (INCI name: silica silylate).

The term "hydrophobic silica" means any silica whose surface is treated with silylating agents, for example halogenated silanes such as alkylchlorosilanes, siloxanes, in particular dimethylsiloxanes such as hexamethyldisiloxane, or silazanes, so as to functionalize the OH groups with silyl groups Si—Rn, for example trimethylsilyl groups.

As regards the preparation of hydrophobic silica aerogel particles surface-modified by silylation, reference may be made to document U.S. Pat. No. 7,470,725.

Use will preferably be made of hydrophobic silica aerogel particles surface-modified with trimethylsilyl groups, preferably of the INCI name Silica silylate.

As hydrophobic silica aerogels that may be used in the invention, examples that may be mentioned include the aerogel sold under the name VM-2260 or VM-2270 (INCI name: Silica silylate), by the company Dow Corning, the particles of which have an average size of about 1000 microns and a specific surface area per unit of mass ranging from 600 to 800 m$^2$/g.

Mention may also be made of the aerogels sold by the company Cabot under the references Aerogel TLD 201, Aerogel OGD 201, Aerogel TLD 203, Enova® Aerogel MT 1100 and Enova Aerogel MT 1200.

Use will preferably be made of the aerogel sold under the name VM-2270 (INCI name: Silica silylate), by the company Dow Corning, the particles of which have an average size ranging from 5-15 microns and a specific surface area per unit of mass ranging from 600 to 800 m$^2$/g.

Preferably, the hydrophobic silica aerogel particles are present in the composition according to the invention in a solids content ranging from 0.1% to 8% by weight, preferably from 0.2% to 5% by weight and preferably from 0.2% to 3% by weight relative to the total weight of the oily phase.

The choice of a silicon derivative or of a modified clay as lipophilic gelling agent proves to be more particularly favoured for preparing cosmetic compositions intended for affording a matting and non-greasy effect with a freshness effect.

Such a gelling agent is particularly advantageous for formulating care and/or makeup compositions intended for greasy to combination skin types.

II. Organopolysiloxane Elastomer

The organopolysiloxane elastomer that may be used as lipophilic gelling agent also has the advantage of giving the composition according to the invention good application properties. It affords a very gentle feel and a matt effect after application, which is advantageous especially for application to the skin, in particular for foundation compositions. It may also allow efficient filling of the hollows present on keratin materials.

The term "organopolysiloxane elastomer" or "silicone elastomer" means a supple, deformable organopolysiloxane with viscoelastic properties and especially with the consistency of a sponge or a supple sphere. Its modulus of elasticity is such that this material withstands deformation and has a limited ability to extend and to contract. This material is capable of regaining its original shape after stretching.

It is more particularly a crosslinked organopolysiloxane elastomer.

Thus, the organopolysiloxane elastomer may be obtained by crosslinking addition reaction of diorganopolysiloxane containing at least one hydrogen bonded to silicon and of diorganopolysiloxane containing ethylenically unsaturated groups bonded to silicon, especially in the presence of a platinum catalyst; or by dehydrogenation crosslinking condensation reaction between a diorganopolysiloxane containing hydroxyl end groups and a diorganopolysiloxane containing at least one hydrogen bonded to silicon, especially in the presence of an organotin; or by crosslinking condensation reaction of a diorganopolysiloxane containing hydroxyl end groups and of a hydrolysable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Preferably, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, especially in the presence (C) of a platinum catalyst, as described, for instance, in patent application EP-A-295 886.

In particular, the organopolysiloxane elastomer may be obtained by reaction of a dimethylpolysiloxane comprising dimethylvinylsiloxy end groups and of methylhydrogenopolysiloxane comprising trimethylsiloxy end groups, in the presence of a platinum catalyst.

Compound (A) is the base reagent for the formation of organopolysiloxane elastomer, and the crosslinking is performed by addition reaction of compound (A) with compound (B) in the presence of the catalyst (C).

Compound (A) is in particular an organopolysiloxane containing at least two hydrogen atoms bonded to different silicon atoms in each molecule.

Compound (A) can exhibit any molecular structure, in particular a linear chain or branched chain structure or a cyclic structure.

Compound (A) can have a viscosity at 25° C. ranging from 1 to 50 000 centistokes, in particular in order to be satisfactorily miscible with compound (B).

The organic groups bonded to the silicon atoms of compound (A) may be alkyl groups such as methyl, ethyl, propyl, butyl, octyl; substituted alkyl groups such as 2-phenylethyl, 2-phenylpropyl or 3,3,3-trifluoropropyl; aryl groups such as phenyl, tolyl, xylyl; substituted aryl groups such as phenylethyl; and substituted monovalent hydrocarbon-based groups such as an epoxy group, a carboxylate ester group or a mercapto group.

Compound (A) can thus be chosen from methylhydrogenopolysiloxanes comprising trimethylsiloxy end groups, dimethyl siloxane-methylhydrogenosiloxane copolymers comprising trimethylsiloxy end groups, and dimethylsiloxane-methylhydrogenosiloxane cyclic copolymers.

Compound (B) is advantageously a diorganopolysiloxane containing at least two lower alkenyl groups (for example $C_2$-$C_4$); the lower alkenyl group may be chosen from vinyl, allyl and propenyl groups. These lower alkenyl groups can be located at any position on the organopolysiloxane molecule but are preferably located at the ends of the organopolysiloxane molecule. The organopolysiloxane (B) can have a branched-chain, linear-chain, cyclic or network structure but the linear-chain structure is preferred. Compound (B) can have a viscosity ranging from the liquid state to the gum state. Preferably, compound (B) has a viscosity of at least 100 centistokes at 25° C.

Besides the abovementioned alkenyl groups, the other organic groups bonded to the silicon atoms in compound (B) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The organopolysiloxanes (B) can be chosen from methylvinylpolysiloxanes, methylvinylsiloxane-dimethylsiloxane copolymers, dimethylpolysiloxanes comprising dimethylvinylsiloxy end groups, dimethylsiloxane-methylphenylsiloxane copolymers comprising dimethylvinyl siloxy end groups, dimethyl siloxane-diphenyl siloxane-methylvinyl siloxane copolymers comprising dimethylvinyl siloxy end groups, dimethylsiloxane-methylvinylsiloxane copolymers comprising trimethylsiloxy end groups, dimethyl siloxane-methylphenyl siloxane-methylvinyl siloxane copolymers comprising trimethyl siloxy end groups, methyl(3,3,3-trifluoropropyl)polysiloxanes comprising dimethylvinyl siloxy end groups, and dimethylsiloxane-methyl(3,3,3-trifluoropropyl)siloxane copolymers comprising dimethylvinylsiloxy end groups.

In particular, the organopolysiloxane elastomer can be obtained by reaction of dimethylpolysiloxane comprising dimethylvinylsiloxy end groups and of methylhydrogenopolysiloxane comprising trimethylsiloxy end groups, in the presence of a platinum catalyst.

Advantageously, the sum of the number of ethylene groups per molecule of compound (B) and of the number of hydrogen atoms bonded to silicon atoms per molecule of compound (A) is at least 5.

It is advantageous for compound (A) to be added in an amount such that the molecular ratio of the total amount of hydrogen atoms bonded to silicon atoms in compound (A) and the total amount of all the ethylenically unsaturated groups in compound (B) is within the range from 1.5/1 to 20/1.

Compound (C) is the catalyst of the crosslinking reaction and is in particular chloroplatinic acid, chloroplatinic acid/olefin complexes, chloroplatinic acid/alkenylsiloxane complexes, chloroplatinic acid/diketone complexes, platinum black and platinum-on-support.

The catalyst (C) is preferably added from 0.1 to 1000 parts by weight, better still from 1 to 100 parts by weight, as platinum metal proper, per 1000 parts by weight of the total amount of compounds (A) and (B).

The elastomer is advantageously a non-emulsifying elastomer.

The term "non-emulsifying" defines organopolysiloxane elastomers not containing any hydrophilic chains, and in particular not containing any polyoxyalkylene units (especially polyoxyethylene or polyoxypropylene) or any polyglyceryl units. Thus, according to one particular mode of the invention, the composition comprises an organopolysiloxane elastomer free of polyoxyalkylene units and of polyglyceryl units.

In particular, the silicone elastomer used in the present invention is chosen from Dimethicone Crosspolymer (INCI name), Vinyl Dimethicone Crosspolymer (INCI name), Dimethicone/Vinyl Dimethicone Crosspolymer (INCI name), Dimethicone Crosspolymer-3 (INCI name).

The organopolysiloxane elastomer particles may be conveyed in the form of a gel formed from an elastomeric organopolysiloxane included in at least one hydrocarbon-based oil and/or one silicone oil. In these gels, the organopolysiloxane particles are often nonspherical particles.

Non-emulsifying elastomers are described especially in patents EP 242 219, EP 285 886 and EP 765 656 and in patent application JP-A-61-194009, the content of which is incorporated herein by way of reference.

The silicone elastomer is generally in the form of a gel, a paste or a powder, but advantageously in the form of a gel in which the silicone elastomer is dispersed in a linear silicone oil (dimethicone) or cyclic silicone oil (e.g.: cyclopentasiloxane), advantageously in a linear silicone oil.

Non-emulsifying elastomers that may be used more particularly include those sold under the names KSG-6, KSG-15, KSG-16, KSG-18, KSG-41, KSG-42, KSG-43 and KSG-44 by the company Shin-Etsu, DC9040 and DC9041 by the company Dow Corning, and SFE 839 by the company General Electric.

According to another alternative, the composition according to the invention may comprise an organopolysiloxane elastomer having the INCI name Polysilicone 11', such as those sold under the name Gransil by Grant Industries.

According to a particular mode, use is made of a gel of silicone elastomer dispersed in a silicone oil chosen from a non-exhaustive list comprising cyclopentadimethylsiloxane, dimethicones, dimethylsiloxanes, methyl trimethicone, phenyl methicone, phenyl dimethicone, phenyl trimethicone and cyclomethicone, preferably a linear silicone oil chosen from polydimethylsiloxanes (PDMS) or dimethicones with a viscosity at 25° C. ranging from 1 to 500 cSt, optionally modified with optionally fluorinated aliphatic groups, or with functional groups such as hydroxyl, thiol and/or amine groups.

Mention may be made especially of the compounds having the following INCI names:

Dimethicone/Vinyl Dimethicone Crosspolymer, such as USG-105 and USG-107A from the company Shin-Etsu; DC9506 and DC9701 from the company Dow Corning;

dimethicone/vinyl dimethicone crosspolymer (and) dimethicone, such as KSG-6 and KSG-16 from the company Shin-Etsu;

dimethicone/vinyl dimethicone crosspolymer (and) cyclopentasiloxane, such as KSG-15;

cyclopentasiloxane (and) dimethicone crosspolymer, such as DC9040, DC9045 and DC5930 from the company Dow Corning;

dimethicone (and) dimethicone crosspolymer, such as DC9041 from the company Dow Corning;

dimethicone (and) dimethicone crosspolymer, such as Dow Corning EL-9240® silicone elastomer blend from the company Dow Corning (mixture of polydimethylsiloxane crosslinked with hexadiene/polydimethylsiloxane (2 cSt)), $C_{4-24}$ alkyl dimethicone/divinyl dimethicone crosspolymer, such as NuLastic Silk MA from the company Alzo.

As examples of silicone elastomers dispersed in a linear silicone oil that may advantageously be used according to the invention, mention may especially be made of the following references:

dimethicone/vinyl dimethicone crosspolymer (and) dimethicone, such as KSG-6 and KSG-16 from the company Shin-Etsu;

dimethicone (and) dimethicone crosspolymer, such as DC9041 from the company Dow Corning; and dimethicone (and) dimethicone crosspolymer, such as Dow Corning EL-9240® silicone elastomer blend from the company Dow Corning.

According to a preferred embodiment, the composition according to the invention comprises at least one crosslinked silicone elastomer having the INCI name 'dimethicone crosspolymer' or 'dimethicone (and) dimethicone crosspolymer', with preferably a dimethicone having a viscosity ranging from 1 to 100 cSt, in particular from 1 to 10 cSt at 25° C., such as the mixture of polydimethylsiloxane crosslinked with hexadiene/polydimethylsiloxane (5 cSt) sold under the name DC 9041 Dow Corning or the mixture of polydimethylsiloxane crosslinked with hexadiene/polydimethylsiloxane (2 cSt) sold under the name Dow Corning EL-9240® silicone elastomer blend Dow Corning.

According to a particularly preferred embodiment, the composition according to the invention comprises at least one crosslinked silicone elastomer having the INCI name: dimethicone (and) dimethicone crosspolymer, with preferably a dimethicone having a viscosity ranging from 1 to 100 cSt, in particular from 1 to 10 cSt at 25° C., such as the mixture of polydimethylsiloxane crosslinked with hexadiene/polydimethylsiloxane (5 cSt) sold under the name DC 9041 Dow Corning.

The organopolysiloxane elastomer particles may also be used in powder form: mention may be made of the powders sold under the names Dow Corning 9505 Powder and Dow Corning 9506 Powder by the company Dow Corning, these powders having the INCI name: dimethicone/vinyl dimethicone crosspolymer.

The organopolysiloxane powder may also be coated with silsesquioxane resin, as described, for example, in U.S. Pat. No. 5,538,793. Such elastomer powders are sold under the names KSP-100, KSP-101, KSP-102, KSP-103, KSP-104 and KSP-105 by the company Shin-Etsu, and have the INCI name: vinyl dimethicone/methicone silsesquioxane crosspolymer.

As preferred lipophilic gelling agents of organopolysiloxane elastomer type, mention may be made more particularly of crosslinked organopolysiloxane elastomers chosen from Dimethicone Crosspolymer (INCI name), Dimethicone (and) Dimethicone Crosspolymer (INCI name), Vinyl Dimethicone Crosspolymer (INCI name), Dimethicone/Vinyl Dimethicone Crosspolymer (INCI name), Dimethicone Crosspolymer-3 (INCI name), and in particular mention be made of Dimethicone Crosspolymer (INCI name).

The organopolysiloxane elastomer may be present in a composition according to the present invention in a content of between 0.5% and 35% by weight of solids and especially between 2% and 15% by weight relative to the total weight of the oily phase.

III. Semi-Crystalline Polymers

The composition according to the invention may comprise at least one semi-crystalline polymer. Preferably, the semi-crystalline polymer has an organic structure, and a melting point of greater than or equal to 30° C.

For the purposes of the invention, the term "semi-crystalline polymer" means polymers comprising a crystallizable portion and an amorphous portion and having a first-order reversible change of phase temperature, in particular of melting (solid-liquid transition). The crystallizable portion is either a side chain (or pendent chain) or a block in the backbone.

When the crystallizable portion of the semi-crystalline polymer is a block of the polymer backbone, this crystallizable block has a chemical nature different than that of the amorphous blocks; in this case, the semi-crystalline polymer is a block copolymer, for example of the diblock, triblock or multiblock type. When the crystallizable portion is a chain that is pendent on the backbone, the semi-crystalline polymer may be a homopolymer or a copolymer.

The melting point of the semi-crystalline polymer is preferably less than 150° C.

The melting point of the semi-crystalline polymer is preferably greater than or equal to 30° C. and less than 100° C. More preferably, the melting point of the semi-crystalline polymer is preferably greater than or equal to 30° C. and less than 70° C.

The semi-crystalline polymer(s) according to the invention are solid at room temperature (25° C.) and atmospheric pressure (760 mmHg), with a melting point of greater than or equal to 30° C. The melting point values correspond to the melting point measured using a differential scanning calorimeter (DSC), such as the calorimeter sold under the name DSC 30 by the company Mettler, with a temperature rise of 5° C. or 10° C. per minute. (The melting point under consideration is the point corresponding to the temperature of the most endothermic peak of the thermogram.)

The semi-crystalline polymer(s) according to the invention preferably have a melting point that is higher than the temperature of the keratinous support intended to receive the said composition, in particular the skin or the lips.

According to the invention, the semi-crystalline polymers are advantageously soluble in the fatty phase, especially to at least 1% by weight, at a temperature that is higher than their melting point. Besides the crystallizable chains or blocks, the blocks of the polymers are amorphous.

For the purposes of the invention, the term "crystallizable chain or block" means a chain or block which, if it were obtained alone, would change from the amorphous state to the crystalline state reversibly, depending on whether one is above or below the melting point. For the purposes of the invention, a "chain" is a group of atoms, which is pendent or lateral relative to the polymer backbone. A block is a group of atoms belonging to the backbone, this group constituting one of the repeating units of the polymer.

Preferably, the polymer backbone of the semi-crystalline polymers is soluble in the fatty phase at a temperature above their melting point.

Preferably, the crystallizable blocks or chains of the semi-crystalline polymers represent at least 30% of the total weight of each polymer and better still at least 40%. The semi-crystalline polymers containing crystallizable side chains are homopolymers or copolymers. The semi-crystalline polymers of the invention containing crystallizable blocks are block or multiblock copolymers. They may be obtained via polymerization of a monomer containing reactive double bonds (or ethylenic bonds) or via polycondensation. When the polymers of the invention are polymers having crystallizable side chains, these side chains are advantageously in random or statistical form.

Preferably, the semi-crystalline polymers of the invention are of synthetic origin.

According to a preferred embodiment, the semi-crystalline polymer is chosen from:
homopolymers and copolymers comprising units resulting from the polymerization of one or more monomers bearing crystallizable hydrophobic side chain(s),
polymers bearing in the backbone at least one crystallizable block,
polycondensates of aliphatic or aromatic or aliphatic/aromatic polyester type,
copolymers of ethylene and propylene prepared via metallocene catalysis, and
acrylate/silicone copolymers.

The semi-crystalline polymers that may be used in the invention may be chosen in particular from:
block copolymers of polyolefins of controlled crystallization, whose monomers are described in EP-A-0 951 897,
polycondensates, especially of aliphatic or aromatic or aliphatic/aromatic polyester type,
copolymers of ethylene and propylene prepared via metallocene catalysis,
homopolymers or copolymers bearing at least one crystallizable side chain and homopolymers or copolymers bearing in the backbone at least one crystallizable block, such as those described in document U.S. Pat. No. 5,156,911, such as the ($C_{10}$-$C_{30}$)alkyl polyacrylates corresponding to the Intelimer® products from the company Landec described in the brochure Intelimer® Polymers, Landec IP22 (Rev. 4-97), for example the product Intelimer® IPA 13-1 from the company Landec, which is a polystearyl acrylate with a molecular weight of about 145 000 and a melting point of 49° C.,
homopolymers or copolymers bearing at least one crystallizable side chain, in particular containing fluoro group(s), as described in document WO-A-01/19333,
acrylate/silicone copolymers, such as copolymers of acrylic acid and of stearyl acrylate bearing polydimethylsiloxane grafts, copolymers of stearyl methacrylate bearing polydimethylsiloxane grafts, copolymers of acrylic acid and of stearyl methacrylate bearing polydimethylsiloxane grafts, copolymers of methyl methacrylate, butyl methacrylate, 2-ethylhexyl acrylate and stearyl methacrylate bearing polydimethylsiloxane grafts. Mention may be made in particular of the copolymers sold by the company Shin-Etsu under the names KP-561 (CTFA name: acrylates/dimethicone), KP-541 (CTFA name: acrylates/dimethicone and isopropyl alcohol), KP-545 (CTFA name: acrylates/dimethicone and cyclopentasiloxane),
and mixtures thereof.

Preferably, the amount of semi-crystalline polymer(s), preferably chosen from semi-crystalline polymers bearing crystallizable side chains, represents from 0.1% to 30% by weight of solids relative to the total weight of the oily phase, for example from 0.5% to 25% by weight, better still from 5% to 20% or even from 5% to 12% by weight, relative to the total weight of the oily phase.

IV. Dextrin Esters

The composition according to the invention may comprise as lipophilic gelling agent at least one dextrin ester.

In particular, the composition preferably comprises at least one preferably $C_{12}$ to $C_{24}$ and in particular $C_{14}$-$C_{18}$ fatty acid ester of dextrin, or mixtures thereof.

Preferably, the dextrin ester is an ester of dextrin and of a $C_{12}$-$C_{18}$ and in particular $C_{14}$-$C_{18}$ fatty acid.

Preferably, the dextrin ester is chosen from dextrin myristate and/or dextrin palmitate, and mixtures thereof.

According to a particular embodiment, the dextrin ester is dextrin myristate, especially such as the product sold especially under the name Rheopearl MKL-2 by the company Chiba Flour Milling.

According to a preferred embodiment, the dextrin ester is dextrin palmitate. This product may be chosen, for example, from those sold under the names Rheopearl TL®, Rheopearl KL® and Rheopearl® KL2 by the company Chiba Flour Milling.

In a particularly preferred manner, the oily phase of a composition according to the invention may comprise from 0.1% to 30% by weight, preferably from 2% to 25% and preferably from 7.5% to 17% by weight of dextrin ester(s) relative to the total weight of the oily phase.

In a particularly preferred manner, the composition according to the invention may comprise between 0.1% and 10% by weight and preferably between 0.5% and 5% by weight of dextrin palmitate relative to the total weight of the oily phase. The dextrin palmitate may especially be the product sold under the names Rheopearl TL®, Rheopearl KL® or Rheopearl® KL2 by the company Chiba Flour Milling.

Hydrophilic Gelling Agent(S)/Lipophilic Gelling Agent(s) Systems

As preferred polymeric hydrophilic gelling agents that are natural or of natural origin, mention may be made more particularly of polysaccharides such as gellans, xanthan gums, kappa-carrageenans and agar-agar, and mixtures thereof.

Advantageously, the lipophilic gelling agent may be chosen from modified clays and especially bentonites and preferably hectorites; waxes, in particular polar waxes, preferably ester waxes and preferably candelilla wax; hydrophobic silica, in particular hydrophobic silica aerogels and preferably silica silylates; dextrin esters and preferably dextrin palmitate; and organopolysiloxane elastomers, and mixtures thereof.

A composition according to the invention may comprise as preferred lipophilic gelling agent at least one organopolysiloxane elastomer or a dextrin ester and/or a particular gelling agent, in particular chosen from a hydrophobic silica, a modified clay and a wax, and mixtures thereof.

As preferred particulate lipophilic gelling agents, mention may be made more particularly of waxes and hydrophobic silicas and especially hydrophobic silica aerogels such as silylated silicas, in particular those sold under the name VM-2270 (INCI name: Silica silylate) by the company Dow Corning.

As preferred lipophilic gelling agents of organopolysiloxane elastomer type, mention may be made more particularly of crosslinked organopolysiloxane elastomers chosen from dimethicone crosspolymer (INCI name), dimethicone (and) dimethicone crosspolymer (INCI name), vinyl dimethicone crosspolymer (INCI name), dimethicone/vinyl dimethicone crosspolymer (INCI name), dimethicone crosspolymer-3 (INCI name), and in particular mention be made of dimethicone crosspolymer (INCI name) and dimethicone (and) dimethicone crosspolymer (INCI name).

According to a particular mode, use is made of a gel of silicone elastomer dispersed in a silicone oil chosen from a non-exhaustive list comprising cyclopentadimethylsiloxane, dimethicones, dimethylsiloxanes, methyl trimethicone, phenyl methicone, phenyl dimethicone, phenyl trimethicone and cyclomethicone, preferably a linear silicone oil chosen from polydimethylsiloxanes (PDMS) or dimethicones with a viscosity at 25° C. ranging from 1 to 500 cSt, especially the following references:

dimethicone/vinyl dimethicone crosspolymer (and) dimethicone, such as KSG-6 and KSG-16 from the company Shin-Etsu;

dimethicone (and) dimethicone crosspolymer, such as DC9041 from the company Dow Corning; and dimethicone (and) dimethicone crosspolymer (INCI name), such as Dow Corning EL-9240® silicone elastomer blend from the company Dow Corning.

According to a particularly preferred embodiment, the composition according to the invention comprises at least one crosslinked silicone elastomer having the INCI name: dimethicone (and) dimethicone crosspolymer, with preferably a dimethicone having a viscosity ranging from 1 to 100 cSt, in particular from 1 to 10 cSt at 25° C., such as the mixture of polydimethylsiloxane crosslinked with hexadiene/polydimethylsiloxane (5 cSt) sold under the name DC 9041 Dow Corning, or the mixture of polydimethylsiloxane crosslinked with hexadiene/polydimethylsiloxane (2 cSt) sold under the name Dow Corning EL-9240® silicone elastomer blend from Dow Corning.

As non-limiting illustrations of hydrophilic gelling agent(s)/lipophilic gelling agent(s) systems that are most particularly suitable for use in the invention, mention may be made of the system of polymeric gelling agent(s) that are natural or of natural origin/particulate gelling agent(s) combined with at least one silicone elastomer or a dextrin ester.

Thus, a composition according to the invention may advantageously comprise as hydrophilic gelling agent(s)/lipophilic gelling agent(s) systems, a system of the type:

gellan gum and xanthan gum/organopolysiloxane elastomer and hydrophobic silica;

kappa-carrageenan and xanthan gum/organopolysiloxane elastomer and hydrophobic silica;

kappa-carrageenan and xanthan gum/dextrin ester combined with a wax;

agar-agar/organopolysiloxane elastomer and hydrophobic silica; or modified or unmodified starches and xanthan gum/organopolysiloxane elastomer.

As stated above, the organopolysiloxane elastomer is preferably chosen from dimethicone crosspolymer, dimethicone (and) dimethicone crosspolymer, vinyl dimethicone crosspolymer, dimethicone/vinyl dimethicone crosspolymer and dimethicone crosspolymer-3.

Aqueous Phase

The aqueous phase of a composition according to the invention comprises water and optionally a water-soluble solvent.

In the present invention, the term "water-soluble solvent" denotes a compound that is liquid at room temperature and water-miscible (miscibility with water of greater than 50% by weight at 25° C. and atmospheric pressure).

The water-soluble solvents that may be used in the composition of the invention may also be volatile.

Among the water-soluble solvents that may be used in the composition in accordance with the invention, mention may be made especially of lower monoalcohols containing from 1 to 5 carbon atoms, such as ethanol and isopropanol, glycols containing from 2 to 8 carbon atoms, such as ethylene glycol, propylene glycol, 1,3-butylene glycol and dipropylene glycol, $C_3$ and $C_4$ ketones and $C_2$-$C_4$ aldehydes.

The aqueous phase (water and optionally the water-miscible solvent) may be present in the composition in a content ranging from 5% to 95%, better still from 30% to 80% by weight and preferably from 40% to 75% by weight relative to the total weight of the said composition.

According to another embodiment variant, the aqueous phase of a composition according to the invention may comprise at least one $C_2$-$C_{32}$ polyol.

For the purposes of the present invention, the term "polyol" should be understood as meaning any organic molecule comprising at least two free hydroxyl groups.

Preferably, a polyol in accordance with the present invention is present in liquid form at room temperature.

A polyol that is suitable for use in the invention may be a compound of linear, branched or cyclic, saturated or unsaturated alkyl type, bearing on the alkyl chain at least two —OH functions, in particular at least three —OH functions and more particularly at least four —OH functions.

The polyols advantageously suitable for the formulation of a composition according to the present invention are those exhibiting in particular from 2 to 32 carbon atoms and preferably from 3 to 16 carbon atoms.

Advantageously, the polyol may be chosen, for example, from ethylene glycol, pentaerythritol, trimethylolpropane, propylene glycol, 1,3-propanediol, butylene glycol, isoprene glycol, pentylene glycol, hexylene glycol, glycerol, polyglycerols such as glycerol oligomers, for instance diglycerol, and polyethylene glycols, and mixtures thereof According to a preferred embodiment of the invention, the said polyol is chosen from ethylene glycol, pentaerythritol, trimethylolpropane, propylene glycol, glycerol, polyglycerols and polyethylene glycols, and mixtures thereof.

According to a particular embodiment, the composition of the invention may comprise at least propylene glycol.

According to another particular embodiment, the composition of the invention may comprise at least glycerol.

Oily Phase

For the purposes of the invention, an oily phase comprises at least one oil.

The term "oil" means any fatty substance that is in liquid form at room temperature and atmospheric pressure.

An oily phase that is suitable for preparing the cosmetic compositions according to the invention may comprise hydrocarbon-based oils, silicone oils, fluoro oils or non-fluoro oils, or mixtures thereof.

The oils may be volatile or non-volatile.

They can be of animal, vegetable, mineral or synthetic origin. According to one embodiment variant, oils of plant origin are preferred.

For the purposes of the present invention, the term "non-volatile oil" means an oil with a vapour pressure of less than 0.13 Pa.

For the purposes of the present invention, the term "silicone oil" means an oil comprising at least one silicon atom, and in particular at least one Si—O group.

The term "fluoro oil" means an oil comprising at least one fluorine atom.

The term "hydrocarbon-based oil" means an oil mainly containing hydrogen and carbon atoms.

The oils may optionally comprise oxygen, nitrogen, sulfur and/or phosphorus atoms, for example in the form of hydroxyl or acid radicals.

For the purposes of the invention, the term "volatile oil" means any oil that is capable of evaporating on contact with the skin in less than one hour, at room temperature and atmospheric pressure. The volatile oil is a volatile cosmetic compound, which is liquid at room temperature, especially having a nonzero vapour pressure, at room temperature and atmospheric pressure, in particular having a vapour pressure ranging from 0.13 Pa to 40 000 Pa ($10^{-3}$ to 300 mmHg), in particular ranging from 1.3 Pa to 13 000 Pa (0.01 to 100 mmHg) and more particularly ranging from 1.3 Pa to 1,300 Pa (0.01 to 10 mmHg).

Volatile Oils

The volatile oils may be hydrocarbon-based oils or silicone oils.

Among the volatile hydrocarbon-based oils containing from 8 to 16 carbon atoms, mention may be made especially of branched $C_8$-$C_{16}$ alkanes, for instance $C_8$-$C_{16}$ isoalkanes (also known as isoparaffins), isododecane, isodecane, isohexadecane and, for example, the oils sold under the trade names Isopar or Permethyl, branched $C_8$-$C_{16}$ esters, for instance isohexyl neopentanoate, and mixtures thereof. Preferably, the volatile hydrocarbon-based oil is chosen from volatile hydrocarbon-based oils containing from 8 to 16 carbon atoms, and mixtures thereof, in particular from isododecane, isodecane and isohexadecane, and is especially isohexadecane.

Mention may also be made of volatile linear alkanes comprising from 8 to 16 carbon atoms, in particular from 10 to 15 carbon atoms and more particularly from 11 to 13 carbon atoms, for instance n-dodecane (C12) and n-tetradecane (C14) sold by Sasol under the respective references Parafol 12-97 and Parafol 14-97, and also mixtures thereof, the undecane-tridecane mixture, mixtures of n-undecane (C11) and of n-tridecane (C13) obtained in Examples 1 and 2 of patent application WO 2008/155 059 from the company Cognis, and mixtures thereof.

Volatile silicone oils that may be mentioned include linear volatile silicone oils such as hexamethyldisiloxane, octamethyltrisiloxane, decamethyltetrasiloxane, tetradecamethylhexasiloxane, hexadecamethylheptasiloxane and dodecamethylpentasiloxane.

Volatile cyclic silicone oils that may be mentioned include hexamethylcyclotrisiloxane, octamethylcyclotetrasiloxane, decamethylcyclopentasiloxane and dodecamethylcyclohexasiloxane.

Non-Volatile Oils

The non-volatile oils may be chosen especially from non-volatile hydrocarbon-based, fluoro and/or silicone oils.

Non-volatile hydrocarbon-based oils that may especially be mentioned include:

hydrocarbon-based oils of animal origin, hydrocarbon-based oils of plant origin, synthetic ethers containing from 10 to 40 carbon atoms, such as dicaprylyl ether, synthetic esters, for instance the oils of formula $R_1COOR_2$, in which $R_1$ represents a linear or branched fatty acid residue containing from 1 to 40 carbon atoms and $R_2$ represents a hydrocarbon-based chain, which is especially branched, containing from 1 to 40 carbon atoms, on condition that $R_1+R_2$ 10. The esters may be chosen especially from fatty alcohol and fatty acid esters, for instance cetostearyl octanoate, isopropyl alcohol esters such as isopropyl myristate or isopropyl palmitate, ethyl palmitate, 2-ethylhexyl palmitate, isopropyl stearate, octyl stearate, hydroxylated esters, for instance isostearyl lactate or octyl hydroxystearate, alkyl or polyalkyl ricinoleates, hexyl laurate, neopentanoic acid esters, for instance isodecyl neopentanoate or isotridecyl neopentanoate, and isononanoic acid esters, for instance isononyl isononanoate or isotridecyl isononanoate, polyol esters and pentaerythritol esters, for instance dipentaerythrityl tetrahydroxy stearate/tetraisostearate, fatty alcohols that are liquid at room temperature, with a branched and/or unsaturated carbon-based chain containing from 12 to 26 carbon atoms, for instance 2-octyldodecanol, isostearyl alcohol and oleyl alcohol, $C_{12}$-$C_{22}$ higher fatty acids, such as oleic acid, linoleic acid, linolenic acid, and mixtures thereof, non-phenyl silicone oils, for instance caprylyl methicone, and phenyl silicone oils, for instance phenyl trimethicones, phenyl dimethicones, phenyltrimethylsiloxydiphenylsiloxanes, diphenyl dimethicones, diphenylmethyldiphenyltrisiloxanes and 2-phenylethyl trimethylsiloxysilicates, dimethicones or phenyl trimethicone with a viscosity of less than or equal to 100 cSt, and trimethyl pentaphenyl trisiloxane, and mixtures thereof; and also mixtures of these various oils.

Preferably, a composition according to the invention comprises volatile and/or non volatile silicone oils. Such silicone oils are particularly appreciated when the oily gelling agent is an organopolysiloxane polymer.

A composition according to the invention may comprise from 5% to 95% by weight, better still from 5% to 40% by weight and preferably from 7% to 35% by weight of oil(s) relative to the total weight of the said composition.

As mentioned above, the gelled oily phase according to the invention may have a threshold stress of greater than 1.5 Pa and preferably greater than 10 Pa. This threshold stress value reflects a gel-type texture of this oily phase.

Dyestuffs

A composition according to the invention may also comprise at least one particulate or non-particulate, water-soluble or water-insoluble dyestuff, preferably in a proportion of at least 0.01% by weight relative to the total weight of the composition.

For obvious reasons, this amount is liable to vary significantly with regard to the intensity of the desired colour effect and to the colour intensity afforded by the dyestuffs under consideration, and its adjustment clearly falls within the competence of a person skilled in the art.

A composition according to the invention may comprise from 0.01% to 15% by weight, especially from 0.1% to 15% by weight, in particular from 1% to 15% by weight and preferably from 5% to 15% by weight of dyestuffs relative to the total weight of the said composition. As stated above, the dyestuffs that are suitable for use in the invention may be water-soluble, but may also be liposoluble.

For the purposes of the invention, the term "water-soluble dyestuff" means any natural or synthetic, generally organic compound, which is soluble in an aqueous phase or in water-miscible solvents, and which is capable of imparting colour.

As water-soluble dyes that are suitable for use in the invention, mention may be made especially of synthetic or natural water-soluble dyes, for instance FDC Red 4, DC Red 6, DC Red 22, DC Red 28, DC Red 30, DC Red 33, DC Orange 4, DC Yellow 5, DC Yellow 6, DC Yellow 8, FDC Green 3, DC Green 5, FDC Blue 1, betanin (beetroot), carmine, copper chlorophylline, methylene blue, anthocyanins (enocianin, black carrot, hibiscus and elder), caramel and riboflavin.

The water-soluble dyes are, for example, beetroot juice and caramel.

For the purposes of the invention, the term "liposoluble dyestuff" means any natural or synthetic, generally organic compound, which is soluble in an oily phase or in solvents that are miscible with a fatty substance, and which is capable of imparting colour.

As liposoluble dyes that are suitable for use in the invention, mention may be made especially of synthetic or natural liposoluble dyes, for instance DC Red 17, DC Red 21, DC Red 27, DC Green 6, DC Yellow 11, DC Violet 2, DC Orange 5, Sudan red, carotenes (β-carotene, lycopene), xanthophylls (capsanthin, capsorubin, lutein), palm oil, Sudan brown, quinoline yellow, annatto and curcumin.

The particulate dyestuffs may be present in a proportion of from 0.01% to 15% by weight relative to the total weight of the composition containing them.

They may especially be pigments, nacres and/or particles with metallic tints.

The term "pigments" should be understood as meaning white or coloured, mineral or organic particles that are insoluble in an aqueous solution, which are intended to colour and/or opacify the composition containing them.

A composition according to the invention may comprise from 0.01% to 15% by weight, especially from 0.1% to 15% by weight, in particular from 1% to 15% by weight and preferably from 5% to 15% by weight of pigments relative to the total weight of the said composition.

The pigments may be white or coloured, and mineral and/or organic.

As mineral pigments that may be used in the invention, mention may be made of titanium oxide, titanium dioxide, zirconium oxide, zirconium dioxide, cerium oxide or cerium dioxide and also zinc oxide, iron oxide or chromium oxide, ferric blue, manganese violet, ultramarine blue and chromium hydrate, and mixtures thereof.

It may also be a pigment having a structure that may be, for example, of sericite/brown iron oxide/titanium dioxide/silica type. Such a pigment is sold, for example, under the reference Coverleaf NS or JS by the company Chemicals and Catalysts, and has a contrast ratio in the region of 30.

They may also be pigments having a structure that may be, for example, of silica microsphere type containing iron oxide. An example of a pigment having this structure is the product sold by the company Miyoshi under the reference PC Ball PC-LL-100 P, this pigment being constituted of silica microspheres containing yellow iron oxide.

Advantageously, the pigments in accordance with the invention are iron oxides and/or titanium dioxides.

The term "nacres" should be understood as meaning iridescent or non-iridescent coloured particles of any shape, especially produced by certain molluscs in their shell or alternatively synthesized, which have a colour effect via optical interference.

A composition according to the invention may comprise from 0 to 15% by weight of nacres relative to the total weight of the said composition.

The nacres may be chosen from nacreous pigments such as titanium mica coated with an iron oxide, titanium mica coated with bismuth oxychloride, titanium mica coated with chromium oxide, titanium mica coated with an organic dye and also nacreous pigments based on bismuth oxychloride. They may also be mica particles at the surface of which are superposed at least two successive layers of metal oxides and/or of organic dyestuffs.

Examples of nacres that may also be mentioned include natural mica coated with titanium oxide, with iron oxide, with natural pigment or with bismuth oxychloride.

Among the nacres available on the market, mention may be made of the nacres Timica, Flamenco and Duochrome (based on mica) sold by the company Engelhard, the Timiron nacres sold by the company Merck, the Prestige mica-based nacres sold by the company Eckart, and the Sunshine synthetic mica-based nacres sold by the company Sun Chemical.

The nacres may more particularly have a yellow, pink, red, bronze, orangey, brown, gold and/or coppery colour or tint.

Advantageously, the nacres in accordance with the invention are micas coated with titanium dioxide or with iron oxide, and also bismuth oxychloride.

For the purposes of the present invention, the term "particles with a metallic tint" means any compound whose nature, size, structure and surface finish allow it to reflect the incident light, especially in a non-iridescent manner.

The particles with a metallic tint that may be used in the invention are in particular chosen from:
  particles of at least one metal and/or of at least one metal derivative;
  particles comprising a monomaterial or multimaterial organic or mineral substrate, at least partially coated with at least one layer with a metallic tint comprising at least one metal and/or at least one metal derivative; and
  mixtures of the said particles.

Among the metals that may be present in the said particles, mention may be made, for example, of Ag, Au, Cu, Al, Ni, Sn, Mg, Cr, Mo, Ti, Zr, Pt, Va, Rb, W, Zn, Ge, Te and Se, and mixtures or alloys thereof. Ag, Au, Cu, Al, Zn, Ni, Mo and Cr and mixtures or alloys thereof (for example bronzes and brasses) are preferred metals.

The term "metal derivatives" denotes compounds derived from metals, especially oxides, fluorides, chlorides and sulfides.

Illustrations of these particles that may be mentioned include aluminum particles, such as those sold under the names Starbrite 1200 EAC® by the company Siberline and Metalure® by the company Eckart and glass particles coated with a metallic layer, especially those described in documents JP-A-09188830, JP-A-10158450, JP-A-10158541, JP-A-07258460 and JP-A-05017710.

Hydrophobic Treatment of the Dyestuffs

The pulverulent dyestuffs as described previously may be totally or partially surface-treated, with a hydrophobic agent, to make them more compatible with the oily phase of the composition of the invention, especially so that they have good wettability with oils. Thus, these treated pigments are well dispersed in the oily phase.

Hydrophobic-treated pigments are described especially in document EP-A-1 086 683.

The hydrophobic-treatment agent may be chosen from silicones such as methicones, dimethicones and perfluoroalkylsilanes; fatty acids, for instance stearic acid; metal soaps, for instance aluminium dimyristate, the aluminium salt of hydrogenated tallow glutamate; perfluoroalkyl phosphates, polyhexafluoropropylene oxides; perfluoropolyethers; amino acids; N-acylamino acids or salts thereof; lecithin, isopropyl triisostearyl titanate, isostearyl sebacate, and mixtures thereof.

The term "alkyl" mentioned in the compounds cited above especially denotes an alkyl group containing from 1 to 30 carbon atoms and preferably containing from 5 to 16 carbon atoms.

Fillers

For the purposes of the present invention, the term "fillers" should be understood as meaning colourless or white solid particles of any form, which are in an insoluble and dispersed form in the medium of the composition.

These fillers, of mineral or organic, natural or synthetic nature, give the composition containing them softness and give the makeup result a matt effect and uniformity.

Preferably, a composition of the invention comprises fillers, particularly when it is dedicated to provide a high coverage.

In particular, a composition according to the invention may comprise from 2% to 35% by weight, especially from 5% to 35% by weight, in particular from 5% to 20% by weight of fillers relative to the total weight of the said composition.

According to one embodiment of the invention, a composition may comprise solid particles such as pigments and/or fillers.

Advantageously, a composition according to the invention may comprise from 0.01% to 25% by weight, especially from 0.1% to 25% by weight, in particular from 1% to 20% by weight and preferably from 5% to 15% by weight of solid particles relative to the total weight of the said composition.

Preferably, when a composition according to the invention is a make-up composition, it may comprise at least 5%, and more preferably at least 10% by weight of solid particles relative to the total weight of the said composition.

Dispersant

Advantageously, a composition according to the invention may also comprise a dispersant.

Such a dispersant may be a surfactant, an oligomer, a polymer or a mixture of several thereof.

According to one particular embodiment, a dispersant in accordance with the invention is a surfactant.

Active Agent

For a particular care application, a composition according to the invention may comprise at least one moisturizer (also known as a humectant).

Preferably, such moisturizer is glycerol.

The moisturizer(s) could be present in the composition in a content ranging from 0.1% to 15% by weight, especially from 0.5% to 10% by weight or even from 1% to 6% by weight, relative to the total weight of the said composition.

As other active agents that may be used in the composition of the invention, examples that may be mentioned include vitamins and sunscreens, and mixtures thereof.

Preferably, a composition of the invention comprises at least one active agent.

It is a matter of routine for those skilled in the art to adjust the nature and amount of the additives present in the compositions in accordance with the invention such that the desired cosmetic properties thereof are not thereby affected.

According to one embodiment, a composition of the invention may advantageously be in the form of a foundation.

According to one embodiment, a composition of the invention may advantageously be in the form of a composition for making up the skin and especially the face. It may thus be an eyeshadow or a face powder.

According to another embodiment, a composition of the invention may advantageously be in the form of a lip product, in particular a lipstick.

According to another embodiment, a composition of the invention may advantageously be in the form of a composition for caring for the skin of the body or the face, in particular the face.

According to another embodiment, a composition of the invention may be in the form of a product for the eyelashes, in particular a mascara.

Such compositions are especially prepared according to the general knowledge of a person skilled in the art.

Throughout the description, including the claims, the term "comprising a" should be understood as being synonymous with "comprising at least one", unless otherwise specified.

The terms "between . . . and . . . " and "ranging from . . . to . . . " should be understood as meaning limits included, unless otherwise specified.

The invention is illustrated in greater detail by the examples and figures presented below. Unless otherwise mentioned, the amounts indicated are expressed as weight percentages.

Methodology for the Oscillating Dynamic Rheology Measurements

These are rheological measurements in the harmonic regime, which measure the elastic modulus.

The measurements are taken using a Haake RS600 rheometer on a product at rest, at 25° C. with a plate-plate rotor Ø 60 mm and a 2 mm gap.

The measurements in the harmonic regime make it possible to characterize the viscoelastic properties of the products. The technique consists in subjecting a material to a stress that varies sinusoidally over time and in measuring the response of the material to this stress. In a region in which the behaviour is linearly viscoelastic (zone in which the strain is proportional to the stress), the stress ($\tau$) and the strain ($\gamma$) are two sinusoidal functions of time that are written in the following manner:

$$\tau(t) = \tau_0 \sin(\omega t)$$

$$\gamma(t) = \gamma_0 \sin(\omega t + \delta)$$

in which:

$\tau_0$ represents the maximum amplitude of the stress (Pa);

$\gamma_0$ represents the maximum amplitude of the strain (–);

$\omega = 2\Pi N$ represents the angular frequency (rad·s$^{-1}$) with N representing the frequency (Hz); and $\delta$ represents the phase angle of the stress relative to the strain (rad).

Thus, the two functions have the same angular frequency, but they are dephased by an angle $\delta$. According to the phase angle $\delta$ between $\tau(t)$ and $\gamma(t)$, the behaviour of the system may be assessed:

if $\delta=0$, the material is purely elastic;

if $\delta=\Pi/2$, the material is purely viscous (Newtonian fluid); and if $0<\delta<\Pi/2$, the material is viscoelastic.

In general, the stress and the strain are written in complex form:

$$\tau^*(t) = \tau_0 e^{i\omega t}$$

$$\gamma^*(t) = \gamma_0 e^{(i\omega t + \delta)}$$

A complex stiffness modulus, representing the overall resistance of the material to the strain, whether it is of elastic or viscous origin, is then defined by:

$$G^* = \tau^*/\gamma^* = G' + iG''$$

in which:

G' is the storage modulus or elastic modulus, which characterizes the energy stored and totally restituted in the course of a cycle, $G' = (\tau_0/\gamma_0) \cos \delta$; and G'' is the loss modulus or viscous modulus, which characterizes the energy dissipated by internal friction in the course of a cycle, $G'' = (\tau_0/\gamma_0) \sin \delta$.

The parameter retained is the mean stiffness modulus G* recorded at the plateau measured at a frequency of 1 Hz.

EXAMPLE 1

Foundation formulations in accordance with the invention are prepared from the phases described below.

1) Preparation of the Aqueous Phase A1

The aqueous phase is prepared from the compounds that follow in the weight proportions stated in the table below.

Phase A1 gives freshness and lightness.

| Phase | Compounds | Weight % Phase A1 |
|---|---|---|
| 1 | Water | qs 100 |
|  | Phenoxyethanol | 1 |
| 2 | Glycerol | 10 |
|  | Xanthan gum | 1.5 |
|  | *Chondrus crispus* powder | 1 |
| 3 | Calcium chloride | 0.075 |
|  | Water | 0.675 |

Phase 2 is prepared at room temperature in a tank equipped with a "deflocculating" paddle, using the compounds mentioned in the above table, in the stated weight proportions.

Phase 3 consists of a solution of calcium chloride dissolved in water at room temperature.

The constituents of phase 1 are placed in a manufacturing tank equipped with a "rotor/stator" turbomixer, with axial and scraping paddles.

The turbomixer stirrer is switched on and phases 2 and 3 are then added with stirring.

The mixture is heated to 75° C. then and stirred until all of the constituents have been totally dispersed.

The mixture is left to cool to 25° C.

The cooling kinetics and the stirring parameters are adjusted as a function of the desired final texture.

| Phase A2 | |
|---|---|
| Compounds | Weight % Phase A2 |
| Water | qs 100 |
| Glycerol | 8.82 |
| Caprylyl glycol | 0.5 |
| Phenoxyethanol | 0.5 |
| Carboxymethyl starch, sodium salt Glycolys ® from the company Roquette | 9.25 |

2) Preparation of the Oily Phases

The oily phases are prepared from the compounds that follow in the weight proportions stated in the tables below.

| Phase B1: | |
|---|---|
| Compounds | Weight % Phase B1 |
| Yellow iron oxide | 4.92 |
| Red iron oxide | 1.00 |
| Black iron oxide | 0.35 |
| Titanium dioxide | 31.24 |
| Isononyl isononanoate | qs 100 |
| Bentone gel (Bentone Gel ISD V ® sold by the company Elementis (87% isododecane/10% disteardimonium hectorite/ 3% propylene carbonate)) | 35.00 (*3.50) |

(*% of disteardimonium hectorite solids)

The pigments are ground with 15% of the ester using a three-roll mill.

The ground material and the remainder of the oil are placed in a beaker and stirred with a Rayneri blender at room temperature.

The gel of bentone in isododecane is added and the mixture is then stirred moderately for 20 minutes, during which time the gel slowly thickens at room temperature.

| Phase B2: | |
|---|---|
| Compounds | Weight % Phase B2 |
| Yellow iron oxide | 4.92 |
| Red iron oxide | 1.00 |
| Black iron oxide | 0.35 |
| Titanium dioxide | 31.24 |
| Pentaerythrityl tetraethylhexanoate | qs 100 |
| Isohexadecane | 21.50 |
| Silica silylate (VM-2270 ® sold by the company Dow Corning) | 6.00 |

| Phase B3: | |
|---|---|
| Compounds | Weight % Phase B3 |
| Yellow iron oxide | 4.92 |
| Red iron oxide | 1.00 |
| Black iron oxide | 0.35 |
| Titanium dioxide | 31.24 |

-continued

| Phase B3: | |
|---|---|
| Compounds | Weight % Phase B3 |
| Isononyl isononanoate | qs 100 |
| C30-50 alcohols (Performacol ® 550 Alcohol sold by the company New Phase Technologies) | 8.00 |
| Polyethylene (Asensa ® SC 211 sold by the company Honeywell) | 2.00 |

The pigments are ground with 15% of the ester using a three-roll mill.
The ground material and the remainder of the oil are placed in a beaker and stirred with a Rayneri blender at room temperature.
The polyethylene and the alcohol wax are added.
The mixture is heated at 95° C. for 25 to 30 minutes.
The mixture is allowed to cool to room temperature.

| Phase B4: | |
|---|---|
| Compounds | Weight % Phase B4 |
| Yellow iron oxide | 4.92 |
| Red iron oxide | 1.00 |
| Black iron oxide | 0.35 |
| Titanium dioxide | 31.24 |
| Isononyl isononanoate | qs 100 |
| C30-45 alkyldimethylsilyl polypropylsilsesquioxane (SW-8005 ® C30 Resin Wax sold by the company Dow Corning) | 7.48 |
| Dextrin palmitate (Rheopearl ® KL2 sold by the company Chiba Flour Milling) | 2.44 |

The pigments are ground with 15% of the ester using a three-roll mill.
The ground material and the remainder of the oil are placed in a beaker and stirred with a Rayneri blender at room temperature.
The wax and the dextrin palmitate are added.
The mixture is heated at 95° C. for 25 to 30 minutes.
The mixture is allowed to cool to room temperature.

3) Preparation of Foundation Formulations
These formulations are obtained by mixing several phases intended to form the foundations in accordance with the invention, in the proportions described below in Table 1.
The combination of the various phases is established as a function of the desired properties.

The texture obtained for formulation 2 has the appearance of a light foam. The texture spreads very well and the makeup deposit is highly covering and homogeneous. The film is comfortable throughout the day.

The texture obtained for formulation 3 is smooth and homogeneous, and appears to have been whipped. It is fresh and very light to take up.

The formulation has good glidance on the skin on application.

The skin finish is unified, non-greasy and sparingly tacky.

Example 2

Care formulations in accordance with the invention are prepared from the phases described below.

1) Preparation of the Aqueous Phase A3
The aqueous phase A3 is prepared from the compounds that follow in the weight proportions stated in the table below.

| Phase A3: | |
|---|---|
| Compounds | Weight % Phase A3 |
| Ammonium polyacryloyldimethyltaurate, ammonium polyacryldimethyltauramide | 1.3 |
| Caprylyl glycol | 0.5 |
| Dimethicone/vinyl dimethicone crosspolymer as a suspension in water (BY29119 ® sold by the company Dow Corning) | 8.67 |
| Glycerol | 13 |
| Propylene glycol | 8.67 |
| Water | qs 100 |
| Carboxymethyl starch, sodium salt | 1.73 |
| Phenoxyethanol | 0.5 |

Phase A3 is obtained by mixing at room temperature all the constituents described in the above table except for the carboxymethyl starch and the dimethicone/vinyl dimethicone solution.

After total dissolution of the constituents in the water, the carboxymethyl starch and the aqueous solution of dimethicone/vinyl dimethicone are then added to the mixture.

2) Preparation of the Oily Phase B5
The oily phase is prepared from the compounds that follow in the weight proportions stated in the table below.

| Phase B5: | |
|---|---|
| Compounds | Weight % Phase B5 |
| Silica silylate (VM-2270 ® sold by the company Dow Corning) | 5.18 |
| 84.5% Dimethicone/15.5% dimethicone crosspolymer (DC9041 ® sold by the company Dow Corning) | 33.09 (5.13*) |

TABLE 1

| Formulations | Technical performance quality(ies) obtained | Weight % Phase A1 | Weight % Phase A2 | Weight % Phase B1 | Weight % Phase B3 | Weight % Phase B4 |
|---|---|---|---|---|---|---|
| Formulation 1 | Granita | | 60.00 | 40.00 | | |
| Formulation 2 | Cream | | 60.00 | | 40.00 | |
| Formulation 3 | Cream freshness | 60.00 | | 40.00 | | |
| Formulation 4 | Cream freshness | 50.00 | | | | 50.00 |

-continued

Phase B5:

| Compounds | Weight % Phase B5 |
|---|---|
| Acrylate copolymer | 0.33 |
| Isostearyl neopentanoate | 36.29 |
| Isononyl isononanoate | 1.75 |
| Hydrogenated polyisobutene | qs 100 |
| Pentaerythrityl tetraethylhexanoate | 3.24 |

(*% of dimethicone crosspolymer solids)

Phase B5 is obtained by mixing in a mixer of "kneader" type, at room temperature, all of the constituents described in the above table in the weight proportions specified therein, until a homogeneous gel is obtained.

3) Preparation of the Care Formulations 5, 6 and 7

These formulations are obtained by mixing phases A3 and B5 at room temperature in a "Kenwood Chef" mechanical kneader equipped with a stirrer of flexible anchor type, in the proportions indicated below in Table 2.

TABLE 2

| Formulations | Weight % Phase A3 | Weight % Phase B5 |
|---|---|---|
| Formulation 5 | 75.00 | 25.00 |
| Formulation 6 | 58.00 | 42.00 |
| Formulation 7 | 40.00 | 60.00 |

Compositions 5 to 7 have properties of smoothing the microrelief via optical effects.

4) Characterization of the Optical Properties

The optical properties of phases A3 and B5 and of formulations 5, 6 and 7 were characterized using the haze measurement (veil or mask effect) with a commercial "Hazemeter" machine.

The measurements were taken according to the following protocol: on a transparent plastic film (Byk), a layer with a wet thickness of 30 μm of the composition whose haze it is desired to evaluate is spread, using an automatic spreader. It is left to dry for 24 hours in an oven at 30° C., and the haze index is then measured using a Byk Gardner brand Haze Gard machine.

The values obtained for phases A3 and B5 are as follows:

| Phases | Measured haze |
|---|---|
| Phase A3 | 46 |
| Phase B5 | 93 |

The haze values measured for formulations 5, 6 and 7 are given in the following table, along with the theoretical values calculated on the basis of the ratios of phases A3 and B5 (for example, the theoretical haze for formulation 5 is calculated in the following manner: 0.75×46+0.25×93).

| Formulations | Measured haze | Theoretical haze |
|---|---|---|
| Formulation 7 | 86 | 74.2 |
| Formulation 6 | 83 | 65.8 |
| Formulation 5 | 71 | 57 |

Irrespective of the composition, the measured haze value is consistently greater than the theoretical value predicted by the ratio of the phases in the sample.

Consequently, the compositions according to the invention show proof of a real synergistic effect.

The invention claimed is:

1. Cosmetic gel/gel type composition, different from an emulsion, for making up and/or caring for keratin materials, comprising:
    at least one aqueous phase gelled with at least one polymeric gelling agent that is natural or of natural origin, being a sodium salt of carboxymethyl starch; and
    at least one oily phase gelled with at least one lipophilic gelling agent that is a mixture of hydrophobic silica chosen from hydrophobic silica aerogels and of organopolysiloxane elastomer chosen from dimethicone crosspolymer, dimethicone (and) dimethicone crosspolymer, vinyl dimethicone crosspolymer, dimethicone/vinyl dimethicone crosspolymer and dimethicone crosspolymer-3;
    the said phases forming therein a macroscopically homogeneous mixture;
    on condition that when the lipophilic gelling agent consists of a trimethyl silica, then the polymeric gelling agent which is natural or of natural origin does not consist of 3% or more of potato carboxymethyl starch.

2. Composition according to claim 1, containing at least one dyestuff.

3. Composition according to claim 1, containing the aqueous and oily phases in an aqueous phase/oily phase weight ratio of from 95/5 to 5/95.

4. Composition according to claim 1, which is in the form of a foundation, a face powder, an eyeshadow, a lipstick, a mascara and/or a care composition.

5. Composition according to claim 1, further comprising volatile and/or non volatile silicone oils.

6. Composition according to claim 1, further comprising a moisturizer.

7. Composition according to claim 1, for making up and/or caring for the skin and/or the lips.

8. Composition according to claim 1, containing at least one dyestuff present at least in the gelled oily phase.

9. Composition according to claim 1, containing the aqueous and oily phases in an aqueous phase/oily phase weight ratio of from 60/40 to 70/30.

10. Process for preparing a gel/gel type cosmetic composition, different from an emulsion, for making up and/or caring for keratin materials, comprising at least one step of mixing:
    at least one aqueous phase gelled with at least one polymeric gelling agent that is natural or of natural origin, being a sodium salt of carboxymethyl starch; and
    at least one oily phase gelled with at least one lipophilic gelling agent that is a mixture of hydrophobic silica chosen from hydrophobic silica aerogels and of organopolysiloxane elastomer chosen from dimethicone crosspolymer, dimethicone (and) dimethicone crosspolymer, vinyl dimethicone crosspolymer, dimethicone/vinyl dimethicone crosspolymer and dimethicone crosspolymer-3;
    under conditions suitable for obtaining a macroscopically homogeneous mixture.

11. Process according to claim 10, in which the mixture is prepared at room temperature.

12. Process according to claim 10, comprising a step of mixing at least three or even more gelled phases.

13. Cosmetic process for making up and/or caring for keratin materials comprising at least one step which consists in applying to the said keratin material a gel/gel type cosmetic composition, different from an emulsion, for making up and/or caring for keratin materials, comprising at least one aqueous phase gelled with at least one polymeric gelling agent that is natural or of natural origin, being a sodium salt of carboxymethyl starch; and at least one oily phase gelled with at least one lipophilic gelling agent that is a mixture of hydrophobic silica chosen from hydrophobic silica aerogels and of organopolysiloxane elastomer chosen from dimethicone crosspolymer, dimethicone (and) dimethicone crosspolymer, vinyl dimethicone crosspolymer, dimethicone/vinyl dimethicone crosspolymer and dimethicone crosspolymer-3; the said phases forming therein a macroscopically homogeneous mixture; on condition that when the lipophilic gelling agent consists of a trimethyl silica or a crosslinked polymer of dimethicone/vinyl dimethicone, then the polymeric gelling agent which is natural or of natural origin does not consist of 3% or more of potato carboxymethyl starch.

\* \* \* \* \*